US010286043B2

(12) United States Patent
Volk

(10) Patent No.: US 10,286,043 B2
(45) Date of Patent: May 14, 2019

(54) COLLAGEN III COMPOSITION AND USES

(71) Applicant: THE TRUSTEES OF THE UNIVERSITY OF PENNSYLVANIA, Philadelphia, PA (US)

(72) Inventor: Susan Volk, Media, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 15/544,960

(22) PCT Filed: Jan. 19, 2016

(86) PCT No.: PCT/US2016/013913
§ 371 (c)(1),
(2) Date: Jul. 20, 2017

(87) PCT Pub. No.: WO2016/118505
PCT Pub. Date: Jul. 28, 2016

(65) Prior Publication Data
US 2018/0015149 A1 Jan. 18, 2018

Related U.S. Application Data

(60) Provisional application No. 62/105,532, filed on Jan. 20, 2015.

(51) Int. Cl.
| A61K 38/39 | (2006.01) |
| C07K 14/78 | (2006.01) |
| A61K 9/00 | (2006.01) |
| A61K 9/06 | (2006.01) |
| A61K 9/70 | (2006.01) |
| A61K 47/10 | (2017.01) |
| A61K 47/34 | (2017.01) |
| D01F 4/00 | (2006.01) |
| D01F 6/62 | (2006.01) |
| D01F 6/66 | (2006.01) |

(52) U.S. Cl.
CPC ............ *A61K 38/39* (2013.01); *A61K 9/0024* (2013.01); *A61K 9/06* (2013.01); *A61K 9/70* (2013.01); *A61K 47/10* (2013.01); *A61K 47/34* (2013.01); *C07K 14/78* (2013.01); *D01F 4/00* (2013.01); *D01F 6/625* (2013.01); *D01F 6/66* (2013.01); *D10B 2509/00* (2013.01)

(58) Field of Classification Search
None
See application file for complete search history.

(56) References Cited

U.S. PATENT DOCUMENTS

| 7,498,299 B2 | 3/2009 | Burchardt et al. |
| 8,298,756 B2 | 10/2012 | Condeelis et al. |
| 8,586,345 B2 | 11/2013 | Simpson et al. |

| 2003/0032143 A1 | 2/2003 | Neff et al. |
| 2011/0178153 A1 | 7/2011 | Chen et al. |
| 2012/0309683 A1 | 12/2012 | Liang et al. |

FOREIGN PATENT DOCUMENTS

| EP | 1315829 B1 | 7/2010 | |
| EP | 2173274 B1 | 3/2011 | |
| WO | WO-9728253 A1 * | 8/1997 | ......... A61L 27/3804 |

OTHER PUBLICATIONS

Machine translation of WO9728253.*
Lou, Rong et al, "Mechanism for adhesion g protein-coupled receptor gpr56-mediated rhoa activation induced by collagen iii stimulation." PLoS ONE (2014) 9(6) e100043.*
Zhao, Liangping et al, "THe effect of rhoa on human umbilical vein endothelial cell migration and angiogenesis in vitro." Oncol. Rep. (2006) 15 p. 1147-1152.*
Menke, Andre et al, "Down-regulation of e-cadherin gene expression by collagen type i and type iii in pancreatic cancer cell lines." Canc. Res. (2001) 61 p. 3508-3517.*
Hirai, Kei-Ichi et al, "The spread of human lung cancer cells on collagens and its inhibition by type iii collagen." Clin. Expl. Metastasis (1991) 9(6) p. 517-527.*
Su, Boxing et al, "Let-7d suppresses growth, metastasis, and tumor macrophage infiltration in renal cell carcinoma by targeting col3a1 and ccl7." Mol. Canc. (2014) 13 p. 206-221.*
Conti, J. A. et al, "THe role of the extracellular matrix in the development of colorectal cancer liver metastases." Clin. Sci. (2004) 106 (supp 50) p2p, entry P3.*
Caracedo, Sergio et al, "The fibroblast integrein alpha11beta1 is induced in a mechanosensitive manner involving activin a and regulates myofibroblast differentiation." J. Biol. Chem. (2010) 285(14) p. 10434-10443.*
International Search Report and Written Opinion for PCT International Application No. PCT/US2016/013913 dated Mar. 29, 2016.
Ajeti, et al., Structural changes in mixed Col I/Col V collagen gels probed by SHG microscopy: implications for probing stromal alterations in human breast cancer, Biomed Opt Express. 2(8) , 2011 ,2307-2316.
Albini, et al., Metastasis signatures: genes regulating tumor-microenvironment interactions predict metastatic behavior, Cancer Metastasis Rev. 27(1) ,2008 ,75-83 (Abstract Only).
Barsky, et a., Increased content of Type V Collagen in desmoplasia of human breast carcinoma, Am J Pathol. 108(3) ,1982 ,276-283.

(Continued)

*Primary Examiner* — Fred H Reynolds
(74) *Attorney, Agent, or Firm* — Saul Ewing Arnstein & Lehr LLP; Kathryn Doyle

(57) ABSTRACT

The invention includes methods of suppressing cancer metastasis and local recurrence in a subject. In one aspect, the method comprises removing the tumor by surgery; and implanting a composition of the invention to the site of the primary tumor. In another aspect, the method comprises implanting a composition of the invention to a cancerous site. The composition comprises a pharmaceutically effective amount of collagen type III.

14 Claims, 26 Drawing Sheets

(56) References Cited

OTHER PUBLICATIONS

Bredfeldt JS, et al., Automated quantification of aligned collagen for human breast carcinoma prognosis, J Pathol Inform. 5(1) ,2014 ,28.
Conklin, et al., Aligned collagen is a prognostic signature for survival in human breast carcinoma, Am J Pathol. 178 (3) ,2011 ,1221-1232.
Conklin, et al., Why the stroma matters in breast cancer: insights into breast cancer patient outcomes through the examination of stromal biomarkers, Cell Adh Migr. 6(3) ,2012 ,249-260.
Deak, et al., Desmoplasia in benign and malignant breast disease is characterized by alterations in level of mRNAs ,coding for types I and III procollagen, Matrix. 11(4) ,1991 ,252-258 (Abstract Only).
Dvorak, et al., Tumor microenvironment and progression, J Surg Oncol. 103(6) ,2011 ,468-474.
Gilkes, et al., Collagen prolyl hydroxylases are essential for breast cancer metastasis, Cancer Res. 73(11) ,2013 ,3285-3296.
Hance, et al., Lung collagen heterogeneity. Synthesis of type I and type III collagen by rabbit and human lung cells in culture, J Clin Invest. 57(1) ,1976 ,102-111.
Iyengar, et al., Adipocyte-derived collagen VI affects early mammary tumor progression in vivo, demonstrating a critical interaction in the tumor/stroma microenvironment, J Clin Invest. 115(5) , 2005 ,1163-1176.
Kakkad, et al., Collagen I fiber density increases in lymph node positive breast cancers: pilot study, J Biomed Opt. 17(11) , 2012 ,116017.
Kelley, et al., Localization of collagen in the rat lung: biochemical quantitation of types I and III collagen in small airways, vessels, and parenchyma, Lung. 167(5) ,1989 ,313-322.
Levental, et al., Matrix crosslinking forces tumor progression by enhancing integrin signaling, Cell. 139(5) ,2009 ,891-906.
Lopez, et al., in situ force mapping of mammary gland transformation, Integr Biol (Camb). 3(9) ,2011 ,910-921.
Lourenço, et al., A high risk of occurrence of sporadic breast cancer in individuals with the 104NN polymorphism of be COL18A1 gene, Breast Cancer Res Treat. 100(3) ,2006 ,335-338.
Lu, et al., The extracellular matrix: a dynamic niche in cancer progression, J Cell Biol. 196(4) ,2012 ,395-406.
Luparello, et al., Aspects of Collagen Changes in Breast Cancer, J. Carcinogene Mutagene ,2013 ,S13.
Lyons, et al., Postpartum mammary gland involution drives progression of ductal carcinoma in situ through collagen and COX-2, Nat Med. 17(9) ,2011 ,1109-1115.
Maller, et al., Collagen architecture in pregnancy-induced protection from breast cancer, J Cell Sci. 126(Pt 18) ,2013 ,4108-4110.
Maskarinec, et al., Mammographic density as a predictor of breast cancer survival: the Multiethnic Cohort, Breast Cancer Res. 15(1) ,2013 ,R7.
Miller, et al., Characterization of metastatic heterogeneity among subpopulations of a single mouse mammary tumor: heterogeneity in phenotypic stability, Invasion Metastasis. 3(1) ,1983 ,22-31 (Abstract Only).
Mori, et al., Characteristic expression of extracellular matrix in subcutaneous adipose tissue development and adipogenesis; comparison with visceral adipose tissue, Int J Biol Sci. 10(8) , 2014 ,825-833.
Olsen, et al., Hepatic stellate cells require a stiff environment for myofthroblastic differentiation, Am J Physiol Gastrointest Liver Physiol. 301(1) ,2011 ,G110-118.
Parra, et al., Association between decreases in type V collagen and apoptosis in mouse lung chemical carcinogenesis: a preliminary model to study cancer cell behavior, Clinics (Sao Paulo). 65(4) ,2010 ,425-432.
Provenzano, et al., Collagen density promotes mammary tumor initiation and progression, BMC Med. 6 ,2008 ,11.
Provenzano, et al., Collagen reorganization at the tumor-stromal interface facilitates local invasion, BMC Med 4(1) ,2006 ,38.
Radisky, et al., Stromal induction of breast cancer: inflammation and invasion, Rev Endocr Metab Disord. 8(3) ,2007 ,279-287.
Robledo, et al., Type IV collagen induces STAT5 activation in MCF7 human breast cancer cells, Matrix Biol.24(7) ,2005 ,469-477 (Abstract Only).
Takeda, et al., Similar, but not identical, modulation of expression of extracellular matrix components during in vitro and in vivo aging of human skin fibroblasts, J Cell Physiol. 153(3) ,1992 ,450-459 (Abstract Only).
Tilbury, et al., Differentiation of Col I and Col III isoforms in stromal models of ovarian cancer by analysis of second harmonic generation polarization and emission directionality, Biophys J. 106(2) ,2014 ,354-365.
Varani, et al., Decreased collagen production in chronologically aged skin: roles of age-dependent alteration in fibroblast function and defective mechanical stimulation, Am J Pathol. 168(6) , 2006 ,1861-1868.
Volk, et al., Diminished type III collagen promotes myofibroblast differentiation and increases scar deposition in cutaneous wound healing, Cells Tissues Organs. 194(1) ,2011 ,25-37.
Volk, et al., Type III collagen regulates osteoblastogenesis and the quantity of trabecular bone, Calcif Tissue Int. 94(6) ,2014 ,621-631.

* cited by examiner

A

B  C

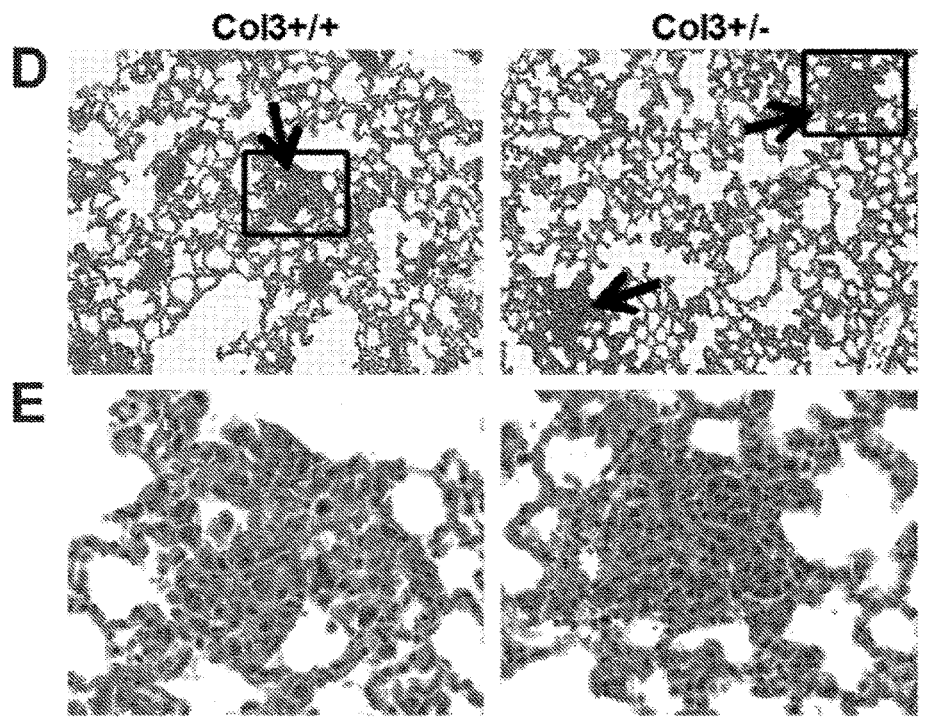
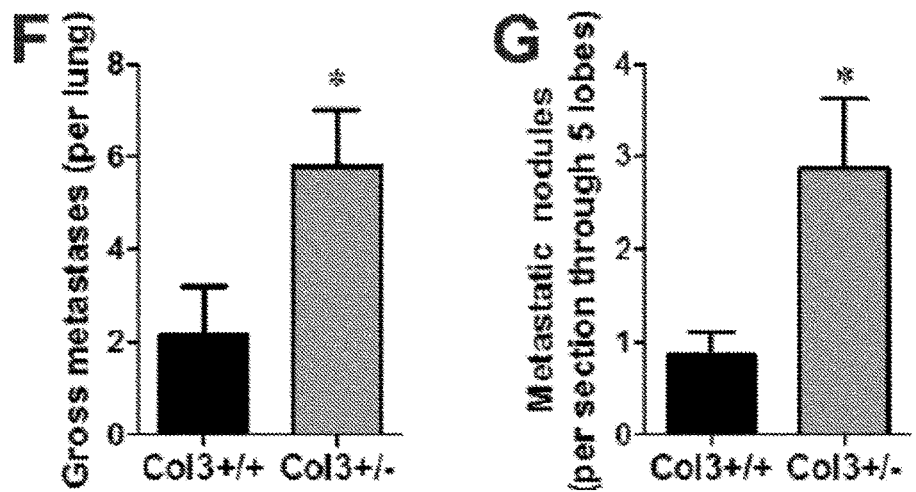
FIGs. 2D-2G

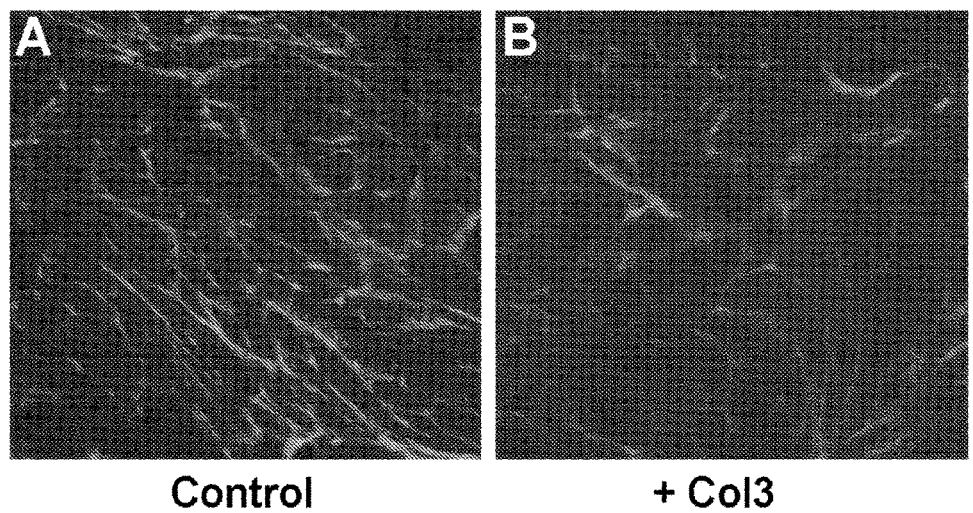
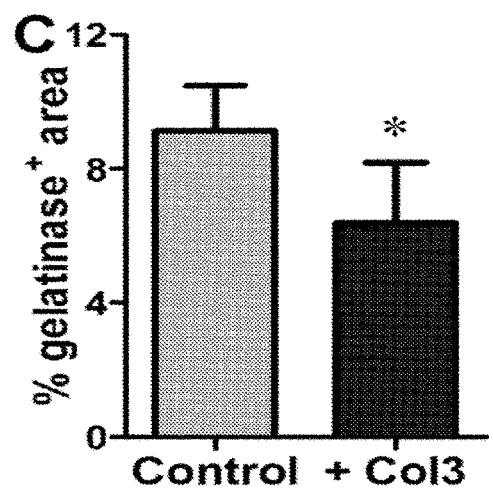
FIGs. 18A-18C

COLLAGEN III COMPOSITION AND USES

CROSS-REFERENCE TO RELATED APPLICATIONS

The present application is a 35 U.S.C. § 371 national phase application from, and claims priority to, International Application No. PCT/US2016/013913, filed Jan. 19, 2016, which claims priority under 35 U.S.C. § 119(e) to U.S. Provisional Application No. 62/105,532, filed Jan. 20, 2015, all of which applications are incorporated herein by reference in their entireties.

STATEMENT REGARDING FEDERALLY SPONSORED RESEARCH OR DEVELOPMENT

This invention was made with government support under grant number AR053945 awarded by the National Institutes of Health. The government has certain rights in the invention.

BACKGROUND OF THE INVENTION

Collagen is the most common structural protein in animals. It is also the most abundant protein in mammals as the main component of connective tissue. Collagen's basic elemental unit is the tropocollagen protein. Tropocollagen is composed of three polypeptide chains of the same size. These chains are wound about each other forming a superhelical cable or a triple-stranded helical rod.

To date, twenty eight types of collagen have been identified and described. The five most common types are types I-V. Collagen type I (Col1) is the most abundant collagen found in the supporting structure of skin tissue, tendon, bone and in the eye cornea. Collagen type II (Col2) is found primarily in particular cartilage, making up about 50% of all cartilage protein. Type III collagen (Col3) is found in many connective tissues throughout the body and its expression is increased during development as well as early in the healing process of a variety of tissues such as bone, tendon, ligament, and skin. Collagen type IV (Col4) is primarily found in basal lamina and eye lens. Collagen type V (Col5) is found in placenta and skin.

Breast cancer is the most frequently diagnosed cancer in women and is the leading cause of cancer-related deaths in women worldwide (World Health Organization: Latest World Cancer Statistics. 2013, Press Release Number 223, http://www.iarc.fr/en/media-centre/pr/2013/pdfs/pr223_E.pdf). In fact, more than 500,000 women are predicted to die in 2015 alone. Without major changes in prevention or treatment, those numbers are anticipated to nearly double in 20 years. In most patients, death is not caused by the primary tumor but rather by metastases. The extracellular matrix (ECM) of the tumor microenvironment plays a critical role in cancer development and progression through its ability to modulate physical, biochemical, and biomechanical cues perceived by both tumor cells and cancer associated stromal cells (Lu P et al., J Cell Biol 2012, 196:395-406; Dvorak H F et al., J Surg Oncol 2011, 103:468-474; Radisky E S et al., Rev Endocr Metab Disord 2007, 8:279-287). However, the mechanistic role that individual stromal components play in regulating tumor cell behavior is largely unknown.

As a major component of the ECM, collagen is increasingly recognized to play a key role in regulating breast cancer progression. While the majority of research on collagen in breast cancer has focused on Col1, and many reports have documented a negative correlation between Col1 expression and prognosis in breast cancer patients (Albini A et al., Cancer Metastasis Rev 2008, 27:75-83), collagens type IV, V, VI and XVIII have also been implicated in modulation of breast cancer cell activities and fate (Luparello C et al., J Carcinogene Mutagene 2013, S13-007; Lourenco G J et al., Breast Cancer Res Treat 2006, 100:335-338; Barsky S H et al., Am J Pathol 1982, 108:276-283; Robledo T et al., Matrix Biol 2005, 24:469-477; Iyengar P et al., J Clin Invest 2005, 115:1163-1176). Increased collagen density in the tumor stroma can promote invasion and metastasis of breast cancer cells (Lyons T R et al., Nat Med 2011, 17:1109-1115; Maskarinec G et al., Breast Cancer Res 2013, 15:R7; Kakkad S M et al., J Biomed Opt 2012, 17:116017). In fact, targeting collagen deposition in the tumor stroma can effectively reduce pulmonary metastasis in breast cancer models (Gilkes D M et al., Cancer Res 2013, 73:3285-3296; Lyons T R et al., Nat Med 2011, 17:1109-1115). In addition, differences in the organization and stiffness of the tumor stroma are known to influence tumor cell responses and stromal remodeling, a key step in metastasis (Provenzano P P et al., BMC Med 2008, 6:11-7015-6-11; Conklin M W et al., Am J Pathol 2011, 178:1221-1232; Ajeti V et al., Biomed Opt Express 2011, 2:2307-2316; Provenzano P P et al., BMC Med 2006, 4:38; Bredfeldt J S et al., J Pathol Inform 2014, 5:28-3539; Tilbury K et al., Biophys J 2014, 106:354-365; Maller 0 et al., J Cell Sci 2013, 126:4108-4110; Levental K R et al., Cell 2009, 139:891-906; Lopez J I et al., Integr Biol (Camb) 2011, 3:910-921; Conklin M W et al., Cell Adh Migr 2012, 6:249-260).

Notwithstanding the progress stated above, there is still a need for new compositions and methods for reducing cancer metastasis and local recurrence. The present invention satisfies this need.

SUMMARY OF THE INVENTION

The present invention relates to a method of suppressing metastasis and local recurrence of a cancer in a subject comprising: a) removing the cancer tumor from the subject; and b) implanting a composition to the site of tumor removed; wherein the composition comprises a pharmaceutically effective amount of collagen type III (Col3). In certain embodiments, Col3 contains a cysteine-rich (CR) domain. In other embodiments, Col3 does not contain a cysteine-rich (CR) domain.

In one embodiment, the cancer is a solid tumor. The solid tumor is selected from the group consisting of fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma. In another embodiment, the cancer is breast cancer. In yet another embodiment, the subject is a human.

In certain embodiments, the collagen type III in the composition is in the range from about 1% to about 100% by weight. In other embodiments, the collagen type III in the composition is in the range from about 20% to about 80% by weight. In yet other embodiments, the collagen type III in the composition is in the range from about 40% to about 60% by weight.

In certain embodiments, the composition further comprises a biocompatible material. The biocompatible material is selected from the group consisting of alginate-poly-(L-lysine), alginate-poly-(L-lysine)-alginate, alginate-poly-(L-lysine)-polyethyleneimine, chitosan-alginate, polyhydroxyethyl-methacrylate-methyl methacrylate, carbonylmethylcellulose, K-carrageenan, chitosan, agarose-polyethersulphone-hexadi-methirine-bromide, ethyl-cellulose, silica gels, hydrogel, (meth)acrylate-oligolactide-PEO-oligolactide-(meth)acrylate, poly(ethylene oxide) (PEO), poly(propylene glycol) (PPO), PEO-PPO-PEO copolymers, poly(phosphazene), poly(methacrylates), poly(N-vinylpyrrolidone), PL(G)A-15 PEO-PL(G)A copolymers, poly(ethylene imine), poly(ethyl glycol) diacrylate, polycaprolactone, and combinations thereof.

In one embodiment, the composition comprises a pharmaceutically effective amount of collagen type III, polycaprolactone, and poly(ethylene oxide) (PEO).

In certain embodiments, the composition is prepared by electrospinning. In certain embodiments, the composition comprising a pharmaceutically effective amount of collagen type III is in a formulation selected from the group consisting of a viscous liquid, a solution, a suspension, a liposomal formulation, a gel, a jelly, a cream, a lotion, an ointment, a suppository, a foam, an aerosol spray, an aqueous suspension, an oily suspension, an aqueous solution, an oily solution, an emulsion, an emulsion ointment, and combinations thereof. In one embodiment, the composition is formulated in a gel.

In one aspect, the invention comprises a method of suppressing metastasis and local recurrence of a cancer in a subject. The method comprises administering a composition to the cancerous site, wherein the composition comprises a pharmaceutically effective amount of collagen type III. In another aspect of the invention, there is provided a method of reducing cancer cell chemoresistance in a subject comprising administering a composition to the cancerous site, wherein the composition comprises a pharmaceutically effective amount of collagen type III.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1A illustrates magnified images (10×) of skin and adjoining subcutaneous fat from fat pads stained with hematoxylin and eosin (H&E). FIG. 1B illustrates serial sections of fat pad from FIG. 1A. Left panel corresponds to isotype control; middle panel corresponds to Col3 stained Col3+/+ tissue sections; and right panel corresponds to Col3 stained Col3+/− tissue sections (and in high magnification images in FIGS. 1C and D). FIG. 1C illustrates magnified images (60×) of Col3-stained dermis. FIG. 1D illustrates magnified images (60×) of Col3-stained fat. FIG. 1E illustrates mRNA expression of Col3 from mammary fat pads (n=4 Col3+/+ and Col3+/−) relative to Col3+/+ fat pads. Data represent means±SEM, *p<0.05. FIG. 1F illustrates 60× images of Col3-stained mammary glands within the mammary fat pad. Scale bars=100 μm.

FIGS. 2A-2H illustrate the finding that orthotopic 4T1 mammary tumor growth and metastasis to the lung is increased in Col3-deficient individuals. FIG. 2A illustrates tumor growth measured in 4T1 tumor bearing ($0.1 \times 10^6$ cells injected) female Col3+/+ and +/− mice (n=7-10 per genotype) using calipers. FIG. 2B illustrates the cumulative pattern of tumor growth. The area under the curve was calculated for each tumor. FIG. 2C illustrates the mass of the tumors determined at the time of sacrifice (day 24). FIG. 2D illustrates H&E sections of lungs from Col3+/+ and +/− mice bearing orthotopic 4T1 tumors (n=7-10 for each genotype). Arrows point to metastatic nodules. FIG. 2E illustrates the magnified view of the box depicted in FIG. 2D. FIG. 2F illustrate the number of gross metastases on lung lobe surfaces from Col3+/+ and +/− mice. FIG. 2G illustrates the number of metastatic nodules within H&E stained sections of all 5 bisected lung lobes of 4T1 tumor-bearing Col3+/+ and Col3+/− mice. FIG. 2H illustrates lung metastatic tumor burden (tumor area over total lung area) calculated from the same images in FIG. 2G using IMAGEJ®. Representative data from five independent experiments with the injection of $0.1$-$5.0 \times 10^6$ cells all showed increased metastases in Col3+/− animals (quantitative data shown following orthotopic injection of $0.1 \times 10^6$ 4T1 cells). Data represent means±SEMs, *p<0.05.

FIG. 4A is a graph illustrating proliferation of 4T1 breast cancer cells on Col3-rich and Col3-null native fibroblast-derived matrices, analyzed using a Brdu cell proliferation assay. Four different littermate embryonic fibroblast pairs (Col3+/+ and −/−) were used to create extracellular matrices. FIG. 4B is a graph illustrating apoptosis of 4T1 cells grown on Col3+/+ and Col3−/− matrices after 48-hr serum-starvation, analyzed by immunofluorescent staining for active Caspase 3. Three littermate embryonic fibroblast pairs (Col3+/+ and −/−) were examined in triplicate (5 images per well). FIG. 4C illustrates primary tumor (4T1) histologic sections from Col3+/+ and +/− mice stained for Ki67 as a marker of proliferating cells. FIG. 4D is a graph illustrating proliferative index (percent Ki67-positive nuclei) calculated from tumors harvested from Col3+/+ and +/− mice. FIG. 4E illustrates tumor sections from Col3+/+ and +/− mice stained for active Caspase 3 as a marker of apoptosis. FIG. 4F is a graph illustrating active Caspase 3 signal (active Caspase 3-positive area) calculated from tumors harvested from Col3+/+ and +/− mice. For both proliferation and apoptosis staining in tumors, five random 20× images that did not contain tumor edge or necrotic regions were taken per tumor (N=7 tumors per genotype). Data represent means±SEM for FIG. 4D and FIG. 4F, *p<0.05.

FIG. 5A is a graph illustrating morphology of 4T1-GFP cells co-cultured with Col3+/+ and −/− fibroblasts in serum-free media for 48 hours. Four different littermate embryonic fibroblast pairs were analyzed (3 representative pairs shown). FIG. 5B illustrates images of 4T1-GFP cells after 2 hours in co-culture with Col3+/+ and −/− fibroblasts. FIG. 5C is a graph illustrating adhesion difference between Col3+/+ and −/− fibroblasts. FIG. 5D is a graph illustrating adhesion difference between Col3, the mixture of Col1 and Col3 (50:50 by weight), Col1, and the mixture of Col1 and Col3 (100:50 by weight). FIG. 5E is a graph illustrating the finding that 4T1 tumor cell adhesion is enhanced in Col3-deficient microenvironments at biologically relevant stiffness. 4T1-GFP cells were allowed to attach for 2 hours to hydrogels (6 kPa) coated with Col3, a 50:50 by weight mixture of Col1:Col3 (Col1/3), or Col1. Attached cells were fixed and GFP fluorescence was read (509 nm). Data represent means±SD, *p<0.05, **p<0.01.

FIG. 6A illustrates images of a basement membrane-like gel (MATRIGEL®) supplemented with Col3, a 50:50 by weight mixture of Col1:Col3 (Col1/3) or Col1, and through a porous membrane, for 16 hours after 4T1 cells were allowed to invade through. FIG. 6B illustrates images of a basement membrane coated by Col3, a 50:50 by weight mixture of Col1:Col3 (Col1/3) or Col1, and through a porous membrane, for 16 hours after 4T1 cells were allowed to invade. FIG. 6C is a graph illustrating quantitative data from experiments examining migration of 4T1 cells (representative image shown in FIG. 6A). FIG. 6D is a graph illustrating quantitative data from experiments examining invasion of 4T1 cells shown in FIG. 6B. Data represent means±SD, *p<0.05.

FIGS. 7A-7I illustrate the finding that Col3 deficiency alters the collagen matrix in fibroblast-derived matrices and the stromal matrix and increases myofibroblast density and alignment in 4T1 mammary tumors. FIG. 7A illustrates images of fibrillar collagen, assessed by Second Harmonic Generation (SHG) imaging, Col3+/+ and −/− fibroblast-derived matrices. White signal represents collagen fibers and illustrates intensity and organization of fibrillar collagen matrices produced by Col3+/+ and −/− fibroblasts. FIG. 7B is a graph illustrating collagen signal intensity (percent SHG-positive area; 5 images taken per individual fibroblast matrix) of Col3+/+ and −/− fibroblast-derived matrices. FIG. 7C illustrates linearity Col3+/+ and −/− fibroblast-derived matrices analyzed by creating FFT plots in IMAGEJ® for each image. The signal that produced a more elongate ellipse shape represents more aligned, organized fibers. FIG. 7D is a graph illustrating the aspect ratio (orientation; length:width of FFT plots) difference as an estimate of collagen fiber alignment between Col3+/+ and −/− decellularized ECM. FIG. 7E illustrates images of H&E sections of 4T1 tumors (harvested from Col3+/+ and Col3+/− mice 14 days after orthotopic injection of 0.5×10⁶ 4T1 cells). FIG. 7F illustrates images obtained by Second Harmonic Generation (SHG) multiphoton microscopy used to visualize the fibrillar collagen in central portions of paraffin embedded 4T1 tumor sections from Col3+/+ and +/− mice. FIG. 7G illustrates images of sections of 4T1 tumors from Col3+/+ and +/− mice (7 per genotype) stained for αSMA, a marker for myofibroblasts. Five random 20× images that did not contain tumor edge, were taken per tumor. Representative images are shown. FIG. 7H is a graph illustrating the differences of myofibroblast density (αSMA+area) in mammary tumors of Col3+/+ and +/− mice. FIG. 7I is a graph illustrating the aspect ratio (orientation/alignment) of the myofibroblasts within tumors of Col3+/+ and +/− mice. Data represent means±SEMs, *p<0.05, p<0.01, *p<0.001.

FIG. 8A is a graph illustrating mRNA expression of Col3 in 14-day tumors (n=4 Col3+/+ and Col3+/−) relative to Col3+/+ tumors. Data represent means±SEM. ns=not significant. FIG. 8B is a set of magnified images (20×) illustrating the heterogeneity in the amount of Col3 staining, but the consistent alignment of the collagen matrix in tumors of Col3+/− mice. FIG. 8C illustrates magnified images (60×) of the Col3-stained tumors in FIG. 8B. Scale bars=100 µm.

FIG. 9A depicts a magnified (2×) H&E stained histologic section of normal mammary fat pad and overlying skin with mammary gland tissue. FIG. 9B depicts the magnified view of the gland tissue shown by arrow in FIG. 9A. FIG. 9C depicts a magnified (2×) H&E stained histologic section of a spontaneous mammary gland carcinoma in a Col3+/− mouse. FIG. 9D depicts magnified view (10×) of the mammary gland carcinoma shown by arrow in FIG. 9C. FIG. 9E depicts a magnified (2×) H&E stained histologic section of a spontaneous mammary gland carcinoma in a Col3+/− mouse. FIG. 9F depicts magnified view (10×) of the mammary gland carcinomas shown by arrow in FIG. 9E. Arrowheads outline the tumor tissue in FIGS. 9A, 9C, and 9E. Bar=200 µm in FIGS. 9A, 9C, and 9E. Bar=400 µm in FIGS. 9B, 9D, and 9F.

FIG. 10A is a graph illustrating adhesion of MDA-MB-231 cells after they were allowed to attach for 2 hours to tissue culture plastic wells coated with Col3, a 50:50 by weight mixture of Col1:Col3 (Col1/3) or Col1. Attached cells were fixed and stained with crystal violet and read at OD 570. FIG. 10B is a graph illustrating invasion of MDA-MB-231 cells after they were allowed to invade through a basement membrane-like gel (MATRIGEL®) supplemented with Col3, a 50:50 by weight mixture of Col1:Col3 (Col1/3) or Col1, and through a porous membrane, for 16 hrs. Cells which had invaded through the gel and the membrane were stained with crystal violet, imaged, and read at OD 570. FIG. 10C is a graph illustrating migration of MDA-MB-231 cells after they were allowed to invade through a basement membrane coated with Col3, a 50:50 by weight mixture of Col1:Col3 (Col1/3) or Col1. Data represent mean±SD of 3 independent experiments; *p<0.05.

FIG. 11A: Second harmonic generation imaging of collagen fibers at the tumor boundary (dotted lines) of 4T1 tumors in Col3+/+ and Col3+/− mice. FIGS. 11B and 11C: Angles of fibers relative to the tumor boundary was analyzed using CurvAlign software. TACS-2 fibers were classified as having angles 0-30 degrees compared to the tumor boundary, while TACS-3 fibers had angles from 60-90 degrees. Data represents N=3 tumors per genotype (average of 4 images per tumor): *, p<0.05; **, p<0.01 via student t-tests.

Figure 13:
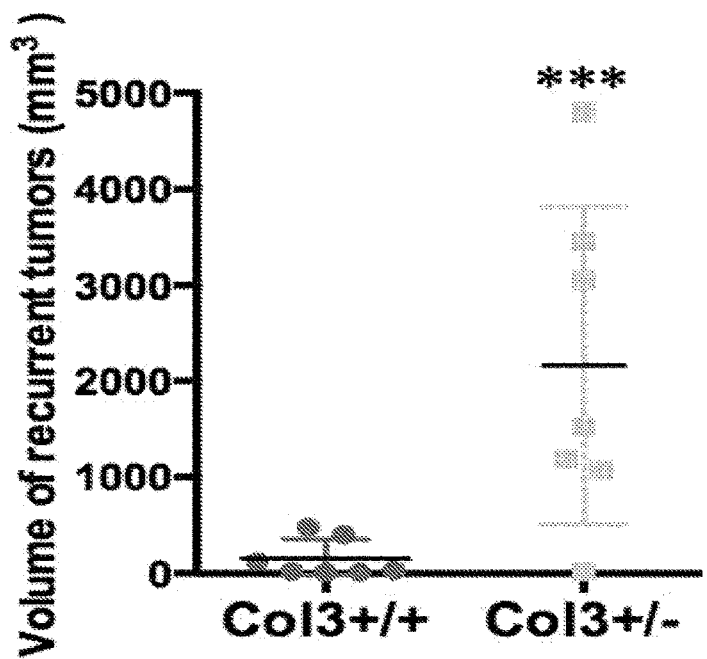

FIG. 13 illustrates the finding that both incidence and volume of local recurrence in Col3+/− mice were significantly greater than that in Col3+/+ mice. FIG. 13 is a graph illustrating that average tumor volume was significantly greater in Col3+/− mice than in Col3+/+ mice; ***$p<0.001$.

Figure 14A:
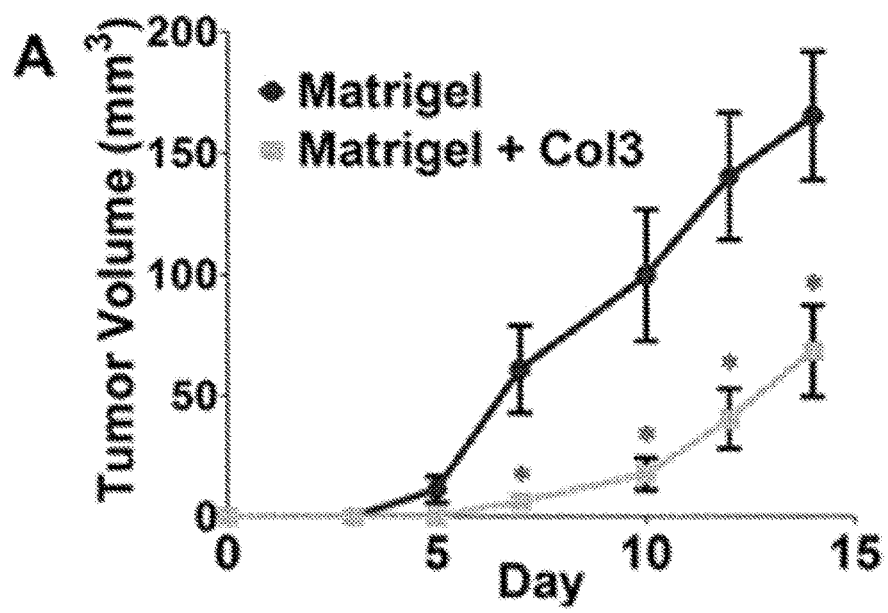
Figures 14B, 14C:
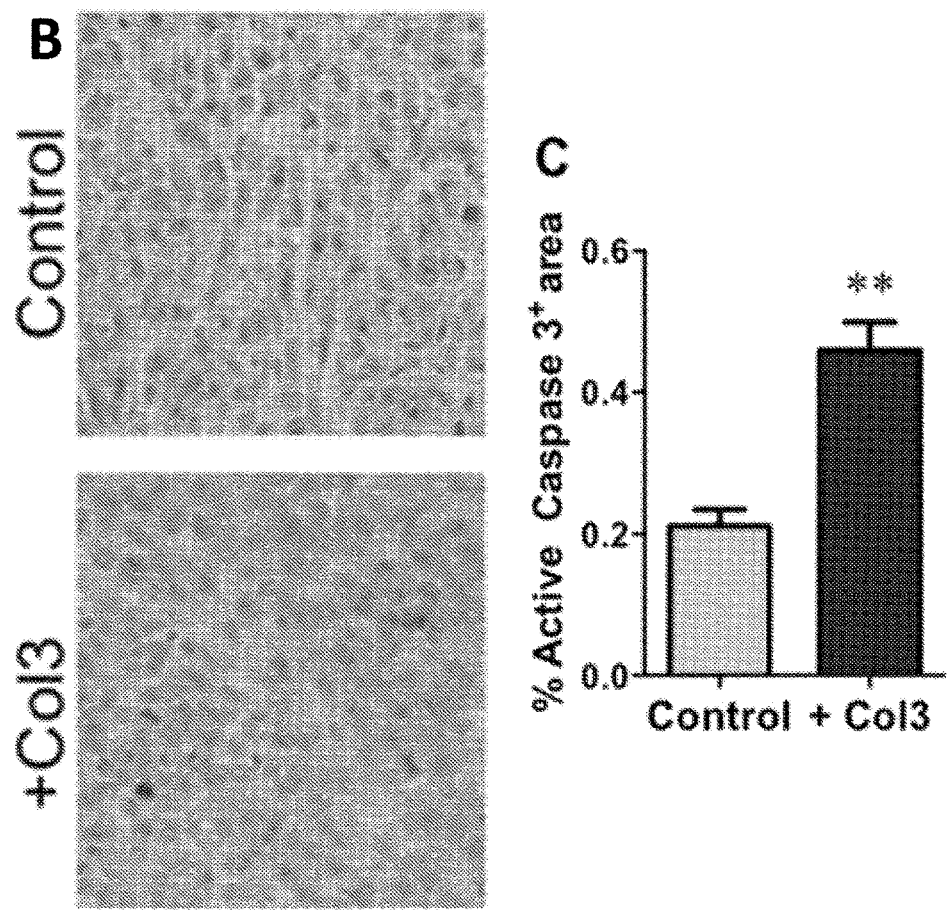

FIGS. 14A-14C illustrate the finding that exogenous Col3 decreases tumor growth and increases apoptosis within the tumor. FIG. 14A is a graph illustrating that inclusion of Col3 during delivery of 4T1 cells in Matrigel decreases primary tumor growth compared to control (Matrigel+vehicle). *$p<0.05$; N=7. A similar finding was observed for MDA-MB-231 tumors orthotopically injected into NOD-Scid mice. FIGS. 14B-14C illustrate the finding that exogenous Col3 increases tumor apoptosis. FIG. 14B illustrates IHC staining for active caspase-3, a marker of apoptosis, in MDA-MB-231 tumors (top panel). FIG. 14B (bottom panel) illustrates IHC staining for active caspase-3, a marker of apoptosis, in tumors with exogenous Col3. FIG. 14C illustrates the finding that Col3 increases tumor cell apoptosis, **$p<0.01$; N=4.

Figure 15A:
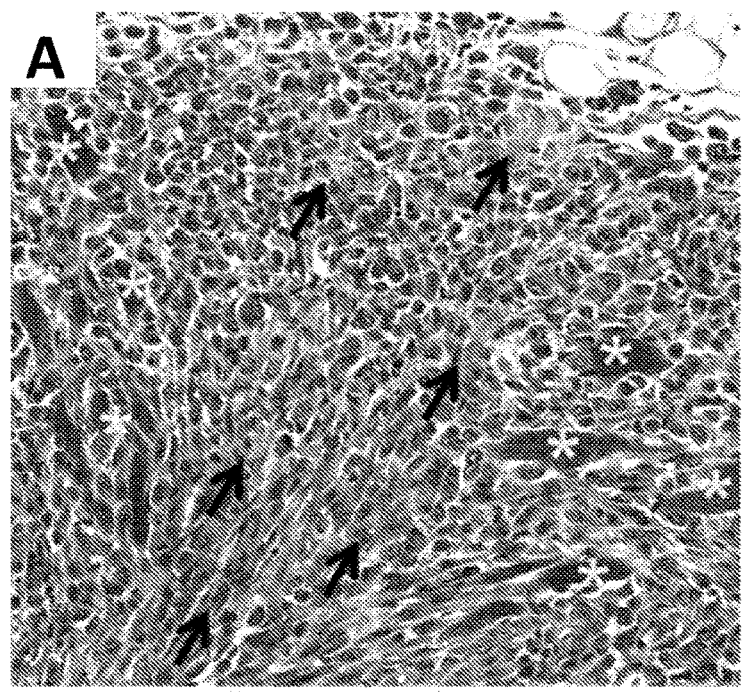
Figure 15B:
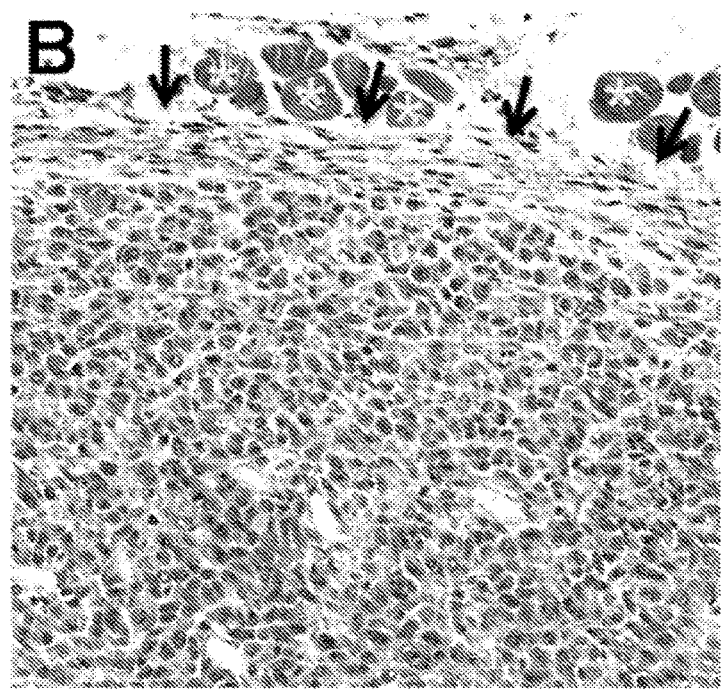

FIGS. 15A and 15B illustrate the finding that exogenous Col3 decreases formation of a tumor permissive matrix and aggressive cancer signatures in MDA-MB-231 tumors in NSG mice. FIG. 15A illustrates Masson's trichrome-stained histologic sections show dense stromal collagen (arrows) aligned with invasion through musculature (asterix) in control tumors (without Col3). FIG. 15B illustrates Masson's trichrome-stained histologic sections showing a tumor restrictive pattern and lack of tumor invasion into the surrounding normal tissues when MDA-MB-231 cells were injected with Col3.

Figures 16A, 16B, 16C, 16D, 16E:
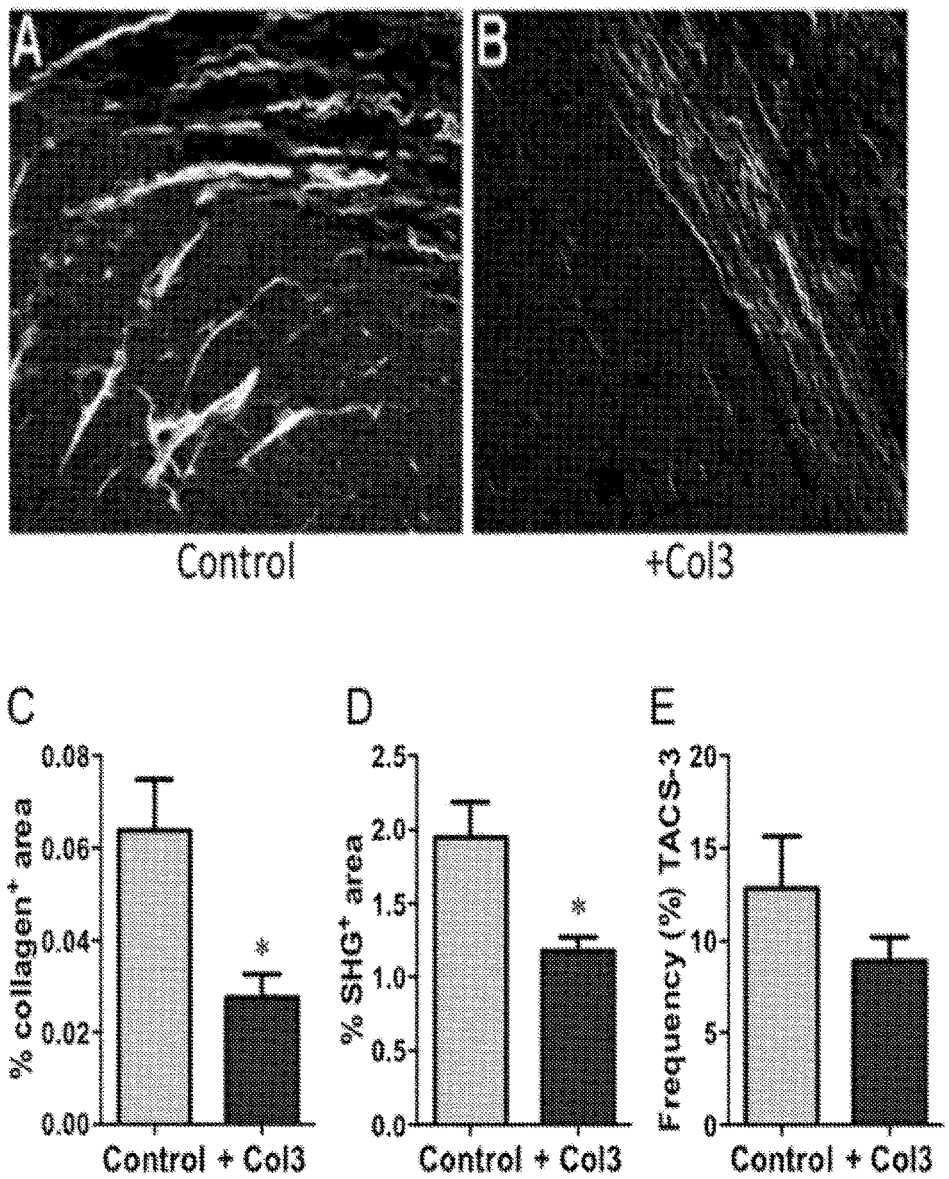

FIGS. 16A-16E illustrate the finding that exogenous Col3 decreases tumor-promoting fibrillar collagen properties. FIG. 16A illustrates a representative SHG image of Control MDA-MB-231 tumors. FIG. 16B illustrates a representative SHG image of a tumor formed when cells were orthotopically implanted in the presence of exogenous Col3. FIGS. 16C and 16D illustrates the finding that Col3 decreases stromal collagen density, assessed using Masson Trichrome stained sections (FIG. 16C) and SHG analysis of histologic sections (FIG. 16D); *$p<0.05$. FIG. 16E illustrates the finding that Col3 decreases TACS-3 frequency.

Figures 17A, 17B, 17C:
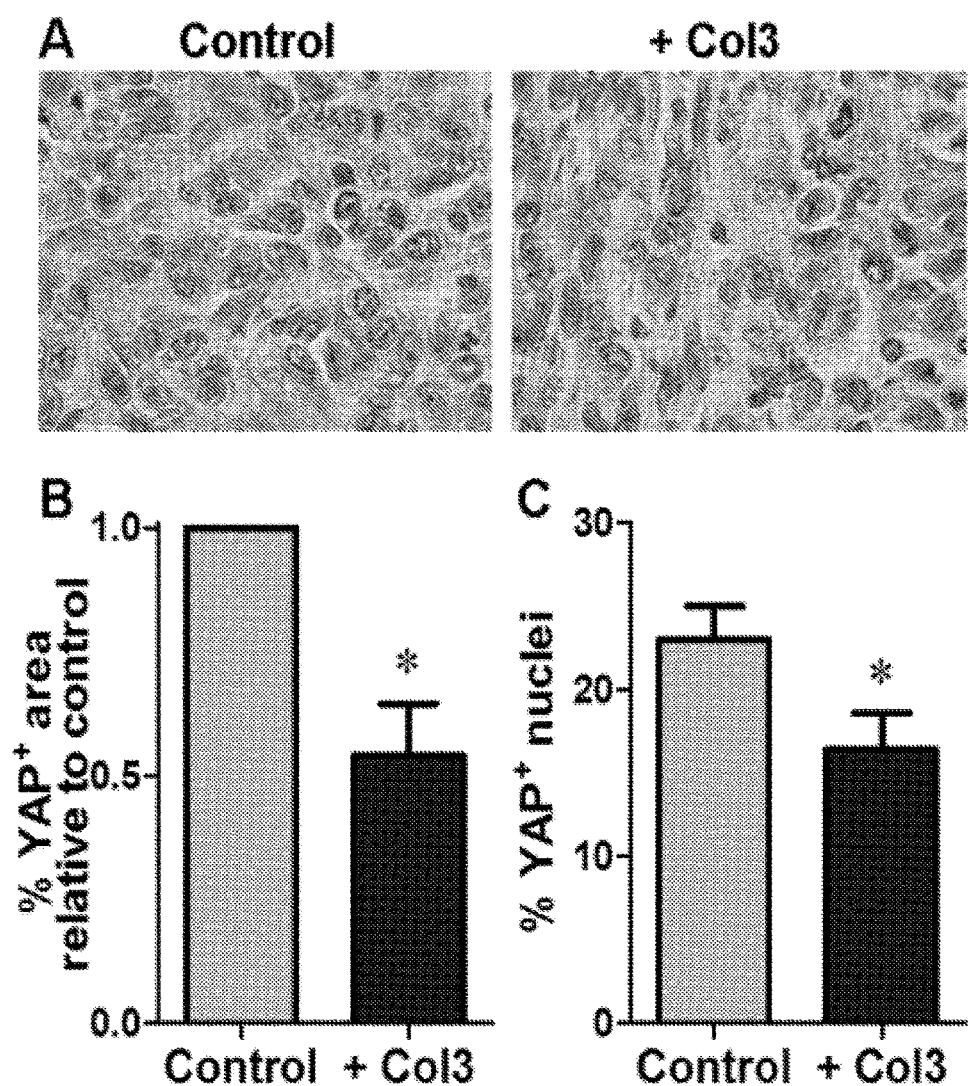

FIGS. 17A-17C illustrate the finding that exogenous Col3 decreases tumor mechanosensing. FIG. 17A illustrates IHC staining for YAP, a mechanosensor, in control MDA-MB-231 tumors and in tumors with exogenous Col3. FIG. 17B illustrates the finding of a decrease in total YAP staining. FIG. 17C illustrates the finding of a decrease in % YAP positive nuclei, *$p<0.05$; N=4.

FIGS. 18A-18C illustrate exogenous Col3 decreases tumor gelatinase activity. FIG. 18A illustrates gelatinase activity, a marker of matrix remodeling, in control MDA-MB-231 by in situ zymography. FIG. 18B illustrates in situ gelatinase activity, a marker of matrix remodeling, in tumors with exogenous Col3. FIG. 18C illustrates the finding that Col3 decreases tumor gelatinase activity, *$p<0.05$; N=4.

Figures 19A, 19B, 19C, 19D, 19E:
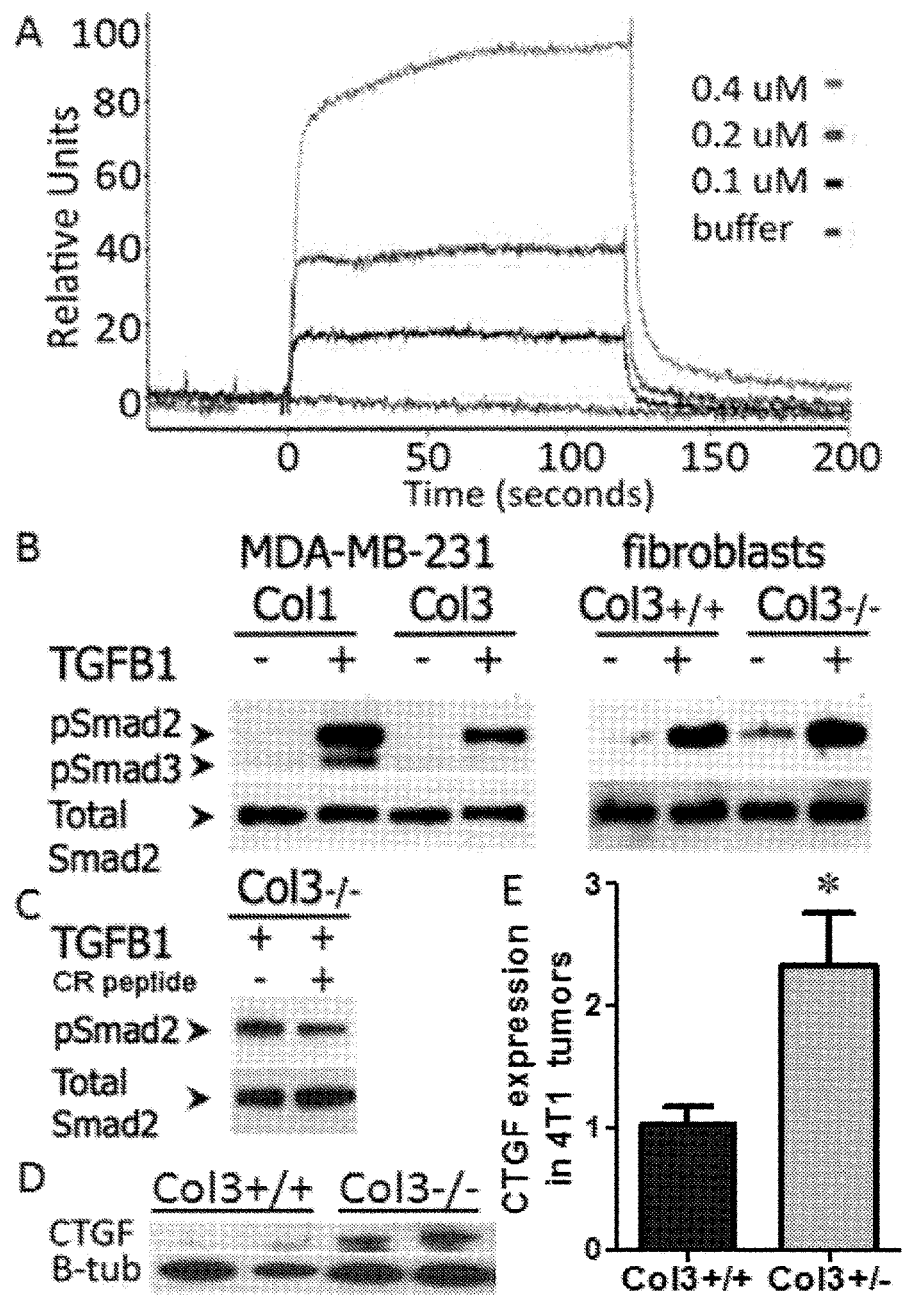

FIGS. 19A-19E illustrate the finding that Col3 suppresses TGFβ signaling and induction of Connective Tissue Growth Factor (CTGF). FIG. 19A illustrates biosensor assay data showing a dose-dependent binding of TGFβ1 to murine cysteine-rich Col3-N-propeptide (CR peptide, expressed in E. coli). FIG. 19B is a western blot illustrating the finding that TGFβ signaling mediator pSmad ⅔ levels are decreased in MDA-MB-231 cells cultured on hpCol3 substratum compared to Col1, as well as in Col3+/+ fibroblasts compared to Col3−/− fibroblasts. FIG. 19C illustrates the finding that the CR peptide attenuates TGFβ signaling in Col3−/− fibroblasts. FIG. 19D is a western blot illustrating the finding that protein levels of CTGF, a downstream mediator of TGFβ signaling, in fibroblasts are increased in Col3-deficiency compared to wild-type controls. FIG. 19E is a bar graph illustrating the finding that expression of CTGF mRNA in 4T1 tumors (day 23 post injection) is increased in Col3-deficient compared to wild-type controls (*$p<0.05$).

Figures 20A, 20B:
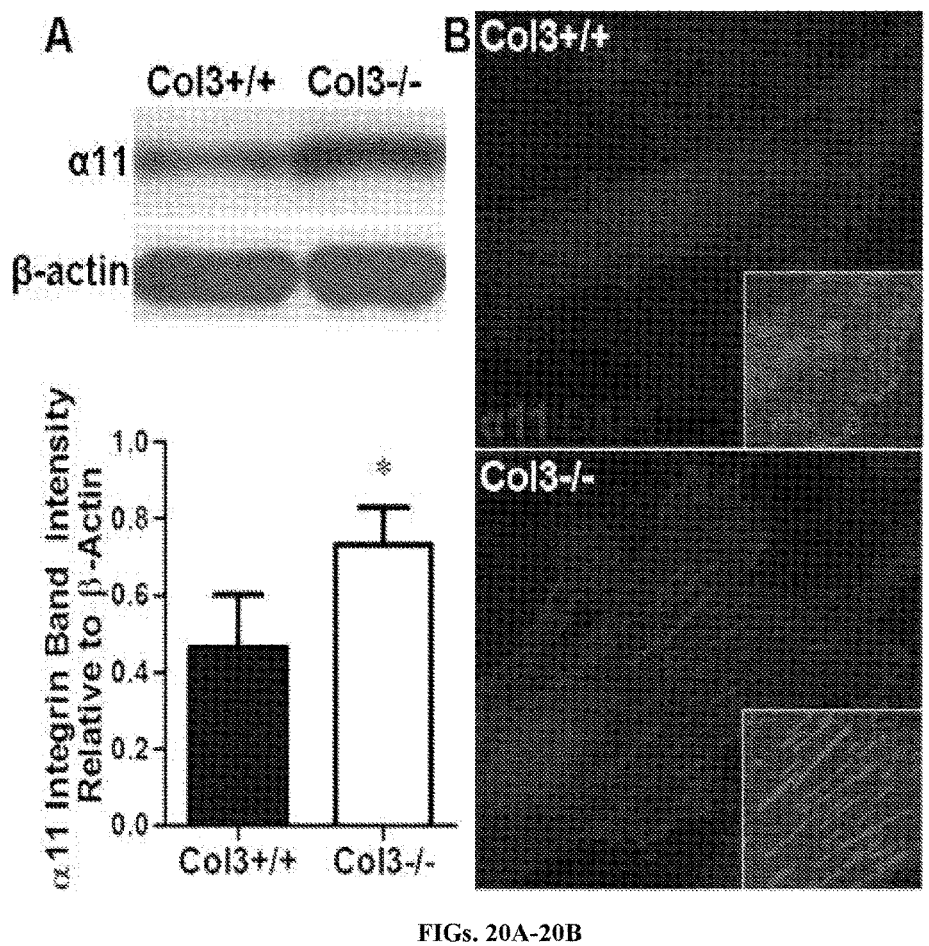

FIGS. 20A-20B illustrate the finding that Col3 suppresses α11 integrin levels. FIG. 20A comprises a western blot and a bar graph illustrating the finding that Col3-deficient fibroblasts up-regulate α11 integrin protein expression, *$p<0.05$. FIG. 20B illustrates immuno-localization of α11 integrin suggesting that α11 clustering at focal adhesions is more efficient in Col3−/− compared to Col3+/+ fibroblasts.

Figure 21:
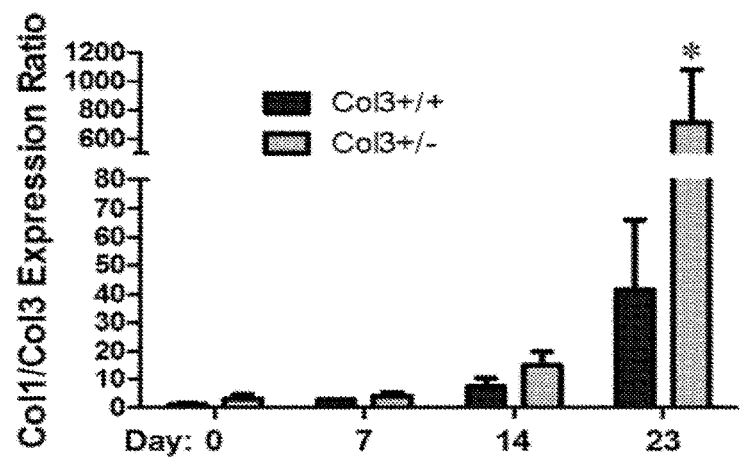

FIG. 21 is a bar graph illustrating the finding that Col1/Col3 ratio is greater in 4T1 tumors in Col3+/− mice than in Col3+/+ mice. mRNA expression of Col1 and Col3 was measured via quantitative real-time PCR in 4T1 tumors generated via orthotopic injection into Col3+/+ and Col3+/− mice. Tumors were harvested for RNA extraction at 0 (fat pad), 7, 14, and 23 days post injection. Data is expressed as Col1 expression verses Col3 expression, normalized to this ratio in Col3+/+ fat pads.

Figures 22A, 22B, 22C, 22D:
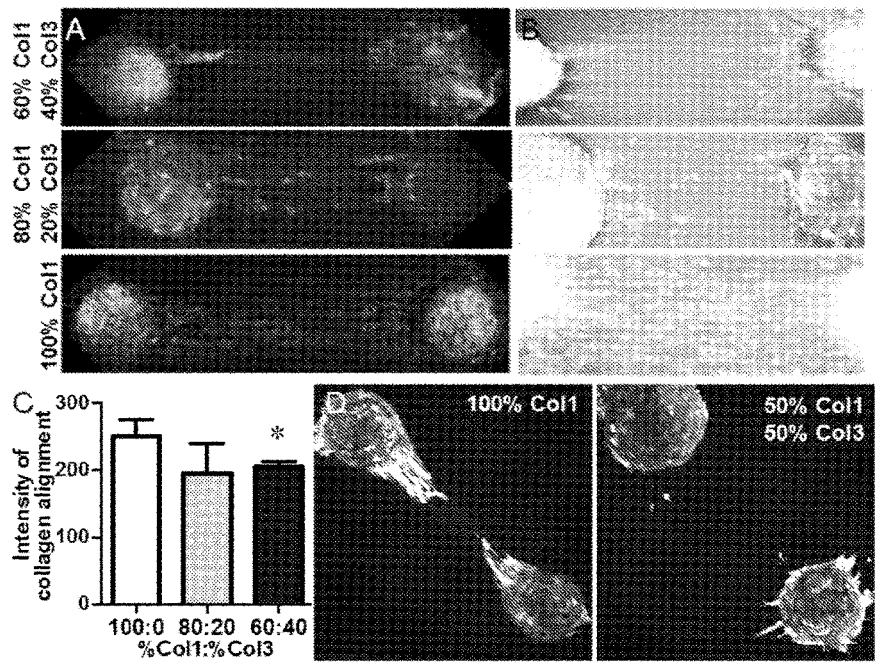

FIGS. 22A-22D illustrate the finding that cells migrated along collagen fibers more readily when Col3 was absent. FIG. 22A is a set of SHG images of NIH 3T3 fibroblast aggregating on 3 mg/ml gels containing mixtures of Col1:Col3 at ratios of 60:40 (top), 80:20 (middle) and 100:0 (no Col3; bottom). FIG. 22B illustrates the finding of an increase in cell migration along the fibers shown with increases exposure. FIG. 22C illustrates the finding that increasing Col3 decreases collagen alignment; *$p<0.05$. FIG. 22D illustrates the finding that 4T1 cell aggregates on Col1 only or 50:50 by weight Col1:Col3 gels suggesting Col3 inhibits cancer cell-mediated collagen alignment and cell migration.

Figures 23A, 23B:
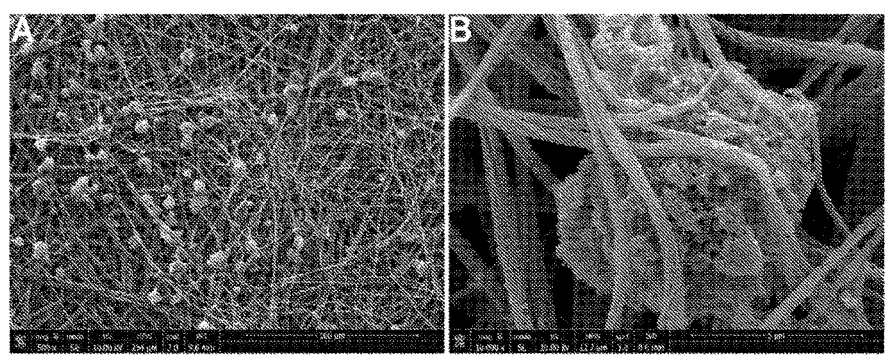

FIGS. 23A-23B illustrate scanning electronic microscopy (SEM) images of 4T1 cells grown on Collagen-coated PCL. FIG. 23A is an SEM image of 4T1 cells grown on Collagen-coated PCL at low magnification (500×). FIG. 23B is an SEM image of 4T1 cells grown on Collagen-coated PCL at high magnification (10,000×). Note thicker fibers in FIG. 23A are PCL fibers, while the thinner fibers are collagen. Collagen striations can be seen in FIG. 23B.

Figures 24A, 24B, 24C:
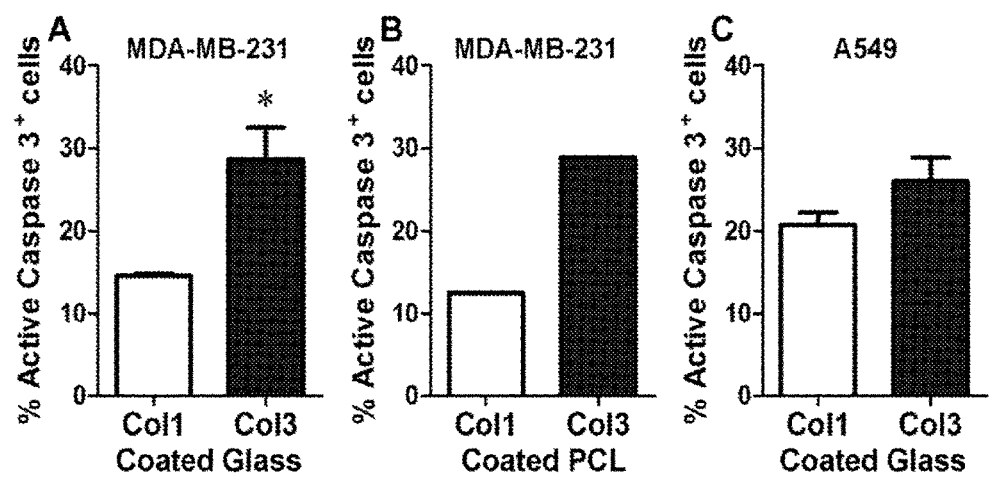

FIGS. 24A-24C illustrate the finding that apoptosis is increased in MDA-MB-231 and A549 cells plated on Col3 compared to Col1. FIG. 24A human mammary tumor MDA-MB-231 cells plated on recombinant collagen-coated glass coverslips. These data illustrate the finding that Col3 induces significantly more apoptosis in response to staurospaurine compared to Col1; *$p<0.05$. FIG. 24B illustrates human mammary tumor MDA-MB-231 cells plated on collagen-coated PCL constructs. FIG. 24C illustrates A549 human lung carcinoma cells plated on recombinant collagen-coated glass coverslips. 1 µM staurosporine, an agent with chemotherapeutic properties, was added to the cells in serum-free media to induce apoptosis for 24 hours. Cells were fixed and stained for active caspase-3, a marker of apoptosis, and positive cells were counted and compared to total cell number.

DETAILED DESCRIPTION OF THE INVENTION

The invention includes methods of suppressing metastasis and local recurrence of a cancer in a subject.

Definitions

As used herein, each of the following terms has the meaning associated with it in this section. Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, and organic chemistry are those well-known and commonly employed in the art.

As used herein, the articles "a" and "an" refer to one or to more than one (i.e. to at least one) of the grammatical object of the article. By way of example, "an element" means one element or more than one element.

As used herein, the term "about" will be understood by persons of ordinary skill in the art and will vary to some extent on the context in which it is used. As used herein when referring to a measurable value such as an amount, a concentration, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

As used herein, the terms "comprising," "including," "containing" and "characterized by" are exchangeable, inclusive, open-ended and does not exclude additional, unrecited elements or method steps. Any recitation herein of the term "comprising," particularly in a description of components of a composition or in a description of elements of a device, is understood to encompass those compositions and methods consisting essentially of and consisting of the recited components or elements.

As used herein, the term "consisting of" excludes any element, step, or ingredient not specified in the claim element.

As used herein, the term "consisting essentially of" does not exclude materials or steps that do not materially affect the basic and novel characteristics of the claim.

The term "effective amount" or "therapeutically effective amount" refers to that amount of a composition described herein that is sufficient to effect the intended application including, but not limited to, disease treatment, as defined below. The therapeutically effective amount may vary depending the subject and disease condition being treated, e.g., the weight and age of the subject, the severity of the disease condition, the manner of administration and the like, which can readily be determined by one of ordinary skill in the art.

As used herein, the terms "metastasis" refers to the spread of a cancer or disease from one organ or part to another.

The term "subject" or "patient" refers to an animal, such as a mammal, for example a human. The methods described herein can be useful in both human therapeutics and veterinary applications.

A "therapeutic effect," as that term is used herein encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

As used herein, the terms "treatment" and "treating" refer to an approach for obtaining beneficial or desired results including, but not limited to, therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

Throughout this disclosure, various aspects of the invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention includes methods of suppressing cancer metastasis and local recurrence in a subject at the primary tumor site. In one aspect, the method comprises: removing the tumor by surgery; and implanting a composition of the invention to the site of the primary tumor. The composition comprises a pharmaceutically effective amount of collagen type III (Col3). In another aspect, the invention includes implanting the composition at the cancerous site without removing the primary tumor.

As demonstrated in the Examples section, Col3 plays a critical role in suppressing cancer metastasis and local recurrence at the primary tumor site. Col3 acts directly as a gate-keeper to invasion within the metastatic niche through effects on tumor cell colonization and survival.

In certain embodiments, Col3 contains a cysteine-rich (CR) domain. In other embodiments, Col3 does not contain a cysteine-rich (CR) domain.

In yet another embodiment, the composition comprises Col3 and a biocompatible material. The biocompatible material that can be used in this invention is selected from the group consisting of alginate-poly-(L-lysine), alginate-poly-(L-lysine)-alginate, alginate-poly-(L-lysine)-polyethyleneimine, chitosan-alginate, polyhydroxylethyl-methacrylate-methyl methacrylate, carbonylmethylcellulose, K-carrageenan, chitosan, agarose-polyethersulphone-hexadi-methirine-bromide, ethyl-cellulose, silica gels, hydrogel, (meth)acrylate-oligolactide-PEO-oligolactide-(meth)acrylate, poly(ethylene oxide) (PEO), poly(propylene glycol) (PPO), PEO-PPO-PEO copolymers, poly(phosphazene), poly(methacrylates), poly(N-vinylpyrrolidone), PL(G)A-15 PEO-PL(G)A copolymers, poly(ethylene imine), poly(ethyl glycol) diacrylate, polycaprolactone, and combinations thereof.

In one embodiment, the composition comprises a pharmaceutically effective amount of collagen type III, polycaprolactone, and poly(ethylene oxide) (PEO). In another embodiment, the composition comprises a pharmaceutically effective amount of collagen type III, polycaprolactone, and poly(ethylene oxide) (PEO), wherein the composition is prepared by electrospinning.

In certain embodiments, the composition is prepared by electrospinning.

The amount of Col3 in the composition can be in the range from about 1% to about 100% by weight. In one instance, the amount of Col3 in the composition is in the range from about 5% to about 95%, about 10% to about 90%, about 15% to about 85%, about 20% to about 80%, about 25% to about 75%, about 30% to about 70%, about 35% to about 65%, or about 40% to about 60% by weight.

In some embodiments, the compositions disclosed herein are in a formulation selected from the group consisting of a viscous liquid, a solution, a suspension, a liposomal formulation, a gel, a jelly, a cream, a lotion, an ointment, a suppository, a foam, an aerosol spray, an aqueous suspension, an oily suspensions, an aqueous solution, an oily solution, an emulsion, an emulsion ointment, and combinations thereof.

In some embodiments, the compositions disclosed herein may take many shapes, such as a bead, a sphere, a cylinder, a capsule, a sheet or any other shape which is suitable for implantation in a subject, and/or culture in an in vitro milieu. The size of the compositions can vary, depending upon its eventual use, as will be clear to the skilled artisan.

Figures 10A, 10B, 10C:
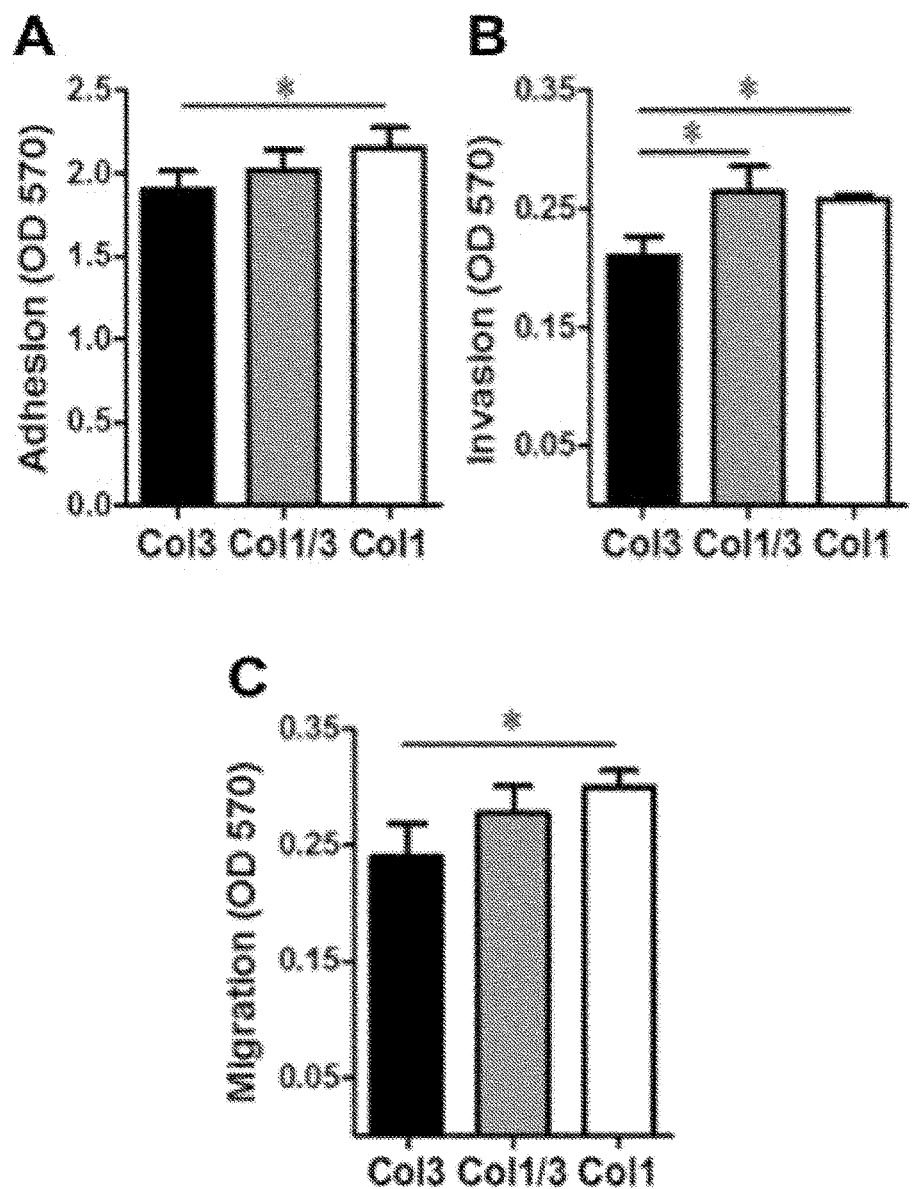
FIGS. 10A-10C illustrate metastatic properties of human breast cancer MDA-MB-231 cells inhibited by the presence of Col3.
Figures 11A, 11B, 11C:
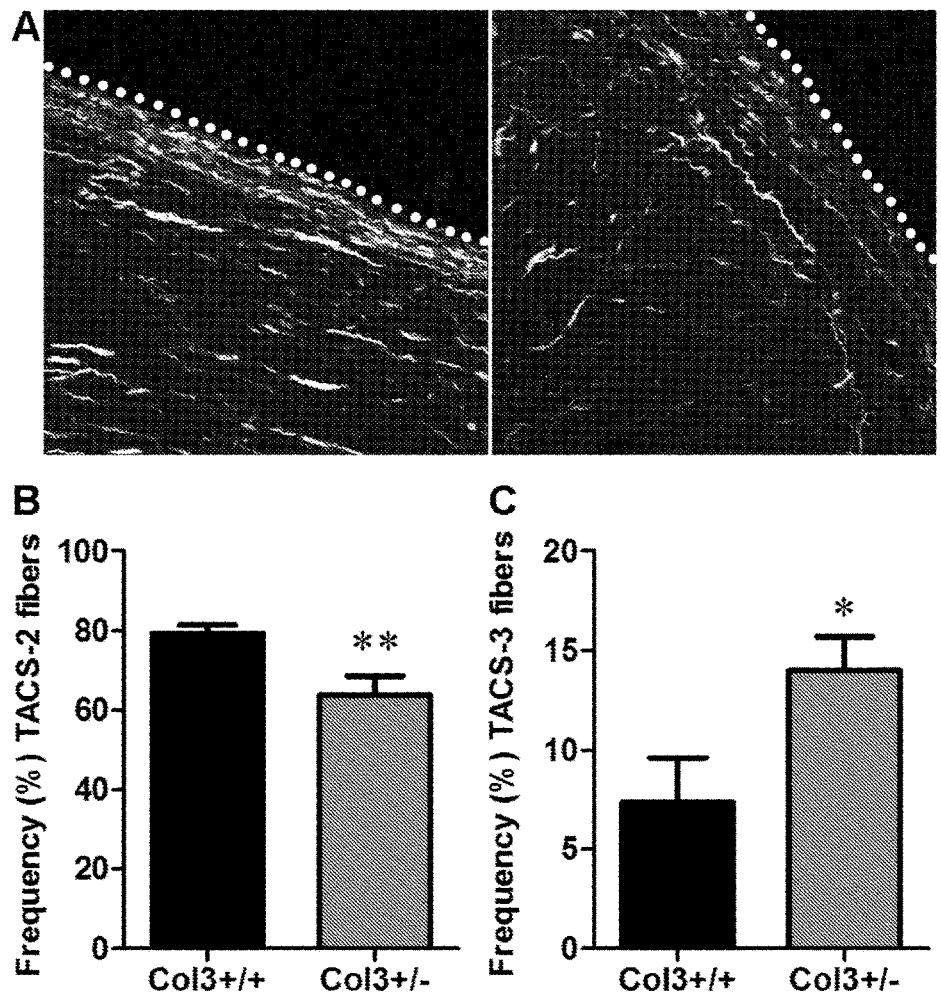
FIGS. 11A-11C illustrate the finding that Col3 deficient tumors contain more collagen fibers perpendicular to the tumor boundary, a more invasive phenotype, than Col3+/+ tumors.

The results in the Examples disclosed herein demonstrate that the collagen matrix from Col3−/− fibroblasts and within tumors of Col3-deficient mice is denser and more highly aligned than in wild-type counterparts (FIGS. 7A-7I). This Col3-deficient matrix promotes a tumor permissive microenvironment (FIGS. 4A-4F, 5A-5E, 6A-6D, 7A-7I, 8A-8C, 10A-10C, and 11A-C) that leads to increased primary tumor growth and metastasis (FIGS. 2A-2H) and local recurrence (FIG. 13). Notably, tumors in Col3+/− mice were found to have significantly increased TACS-3 signatures compared to those from wild-type littermates (FIGS. 11A-11C). TACS-3 has been previously shown to correlate with invasive tumor behavior and poor prognosis in women, as well as murine models (Provenzano P P, BMC Med 2008, 6:11-7015-6-11; Conklin M W et al., Am J Pathol 2011, 178:1221-1232; Provenzano P P et al., BMC Med 2006, 4:38; Bredfeldt J S et al., J Pathol Inform 2014, 5:28-3539; Conklin M W et al., Cell Adh Migr 2012, 6:249-260).

The Examples disclosed herein also demonstrate that Col 3 plays a role in regulating collagen organization both in vitro and in vivo. A reduction in Col3 results in a robust and aligned SHG signal (FIGS. 7A-7I). The density and alignment of αSMA positive myofibroblasts increase in tumors of Col3-haploinsufficient mice. This increase in myofibroblasts may be secondary to Col3 modulation of myofibroblast recruitment, increased proliferation or attenuated apoptosis, or a combination of these processes.

Without being bound by a specific theory, it is hypothesized that the ability of Col3 to decrease collagen network organization likely contributes to its ability to suppress tumor progression and is supported by a significant increase in TACS-3 score development in Col3-deficient (Col3+/−) mice. In support of Col3 serving as a "gatekeeper" to prevent cancer cell escape from the primary tumor, the results from in vitro assays reveal significant Col3-dependent reductions in adhesion, invasion and migration (FIG. 5A-5E and FIG. 6A-6D). Similar Col3-dependent suppressive effects on these metastatic processes were found in the human MDA-MB-231 breast cancer cells (FIG. 10A-10C).

Although the compositions disclosed herein have been tested for their suppressive effects on breast cancer metastasis and local recurrence, the use of the compositions is not limited to any particular cancer. Preferably, the compositions disclosed herein are useful as a treatment for solid tumors.

Examples of solid tumors that can be treated according to the invention include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

In one embodiment, the subject is a human.

In yet another aspect, the invention relates to a method of determining whether one antifibrotic used as adjuvant therapy for a cancer patient is more effective than another antifibrotic used as adjuvant therapy. The method comprises testing the effect of the antifibrotics on the Col1 and Col3 expression; and identifying the antifibrotic which preferentially decreases Col1 expression but not Col3 expression as being a more effective adjuvant therapy for cancer treatment.

Adjuvant therapy, also called adjuvant care, is treatment that is given in addition to the primary, main or initial treatment. In certain embodiments, the primary treatment is removing the cancerous cells or solid tumor. An antifibrotic is a drug or a treatment that acts to inhibit or reduce fibrosis. Methods of testing the effect of an antifibrotic on the Col1 and Col3 expression are well known in the art. Since Col1 is associated with a poor prognosis for many tumors including breast cancer, and decreasing fibrosis has been shown to improve outcomes, many antifibrotics are known to decrease Col1. However, most of the antifibrotics do not discriminate between Col1 and Col3. Based on findings of the present invention that Col3 suppresses breast cancer metastasis and local recurrence, an antifibrotic that preferentially decrease Col1 expression but not Col3 expression should be more effective in improving prognosis.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials and Methods

Col3-Deficient Mice

Animal utilization and care was approved by the Institutional Animal Care and Use Committee (IACUC) of the University of Pennsylvania and followed guidelines set forth in the National Institutes of Health (NIH) Guide for the Care and Use of Laboratory. All mice for this study were generated in a colony established at the University of Pennsylvania from breeder pairs of Col3α1 heterozygous (Col3+/−) mice originally purchased from Jackson Laboratories (Bar Harbor, Me., USA). These mice had been generated by homologous recombination by replacement of the promoter region and first exon of the Col3 gene with a 1.8-kb PGKneo cassette, creating a global knockout. Animals were genotyped for Col3 by PCR analysis of DNA extracted from tail biopsies and were micro-chipped for identification (Allflex FDX-B transponders; Allflex USA, Inc., Dallas, Tex.) (Volk S W et al, Cells Tissues Organs 2011, 194:25-37; Volk S W et al., Calcif Tissue Int 2014, 94:621-631).

All mice in the Col3 colony, regardless of the study they were used for, were surveyed routinely for general health and pathology, including gross evidence of tumor development. Once a trend was recognized for an increase in tumor formation in Col3+/− mice, all mice dying spontaneously or euthanized at greater than one year of age had a gross necropsy performed and any abnormal masses were biopsied. Histopathologic diagnoses of biopsied tumors were made by a board-certified veterinary pathologist.

Cell Culture and Tumor Generation

4T1 and 4T1-GFP cell lines (Aslakson C J et al., Cancer Res 1992, 52:1399-1405) and MDA-MB-231 cells (Peng H et al., Cancer Res 2014, 74:1390-1403) were authenticated by morphology, growth characteristics and biologic behavior (4T1s), tested for mycoplasma and frozen. Cells were cultured for less than 4 months. All cells were cultured in growth media: Dulbecco's Modified Eagle Medium (DMEM; Glutamax; Gibco, Grand Island, N.Y.) supplemented with 10% fetal bovine serum (FBS; Atlanta Biologicals, Flowery Branch, Ga.) and antibiotics (100 U/ml penicillin and 100 g/ml streptomycin). GFP expression in the 4T1-GFP cell line was preserved with inclusion of 50 ug/mL G418 in the growth media.

For orthotopic tumor implantation, 0.1 or $0.5 \times 10^6$ 4T1 cells (in 0.1 mL sterile phosphate buffered saline (PBS)) were injected subcutaneously into the right $4^{th}$ mammary fat pad of anesthetized mice (8-20 weeks old). Tumor volume was calculated using the formula $V=(L \times W^2)/2$ (Egunsola A T et al., Cell Immunol 2012, 272:220-229).

Tissue Processing

Primary tumors, mammary fat pads, and lungs were collected and fixed in Prefer Fixative (Anatech LTD, Battle Creek, Mich.). Prior to fixation, lungs were perfused through the heart and trachea. Tissues were paraffin embedded, processed, and serial 4-µm sections were stained with hematoxylin and eosin (H&E) as previously described (Volk S W et al., Cells Tissues Organs 2011, 194:25-37).

Analysis of Pulmonary Metastases

After perfusion and fixation, gross lung metastases in mice with orthotopic 4T1 tumors were counted. All lung lobes were bisected lengthwise through the main stem bronchi (Leustik M et al., Am J Physiol Lung Cell Mol Physiol 2008, 295:L733-43). Quantitation of metastasis on H&E stained-slides containing a cross section of all five lung lobes was performed by a pathologist (E.A.M.). Lung tumor burden was quantitated using IMAGEJ® (NIH, Bethesda, Md.), as previously described (Santos A M et al., J Clin Invest 2009, 119:3613-3625).

Tissue Immunohistochemistry and Immunofluorescence (IHC and IF)

Sections from fixed, paraffin-embedded tissues were mounted on charged glass slides. After deparaffinization and rehydration, antigen retrieval was performed by citrate buffer boiling or incubation with proteinase K (20 µg/mL in Tris-ethylenediaminetetraacetic acid (TE) buffer for Col3 staining). For IHC, sections were blocked in: 3% $H_2O_2$, PBS containing 1% bovine serum albumin (BSA,A5611; Sigma-Aldrich, St. Louis, Mo.) and 10% goat serum, Avidin Blocking solution, and Biotin blocking solution (Avidin Blocking Kit; Vector Laboratories Inc., Burlingame, Calif.). For IF, sections were blocked in PBS containing 5% BSA, 5% goat serum, and 0.05% Tween-20 (Bio-Rad, Hercules, Calif.). Slides were incubated with antibodies directed against Col3 (ab7778; Abcam, Cambridge, Mass.), Ki67 (ab15580; Abcam), active Caspase 3 (9664; Cell Signaling, Danvers, Mass.) or alpha Smooth Muscle Actin (αSMA; ab5694; Abcam). For IHC, slides were incubated in secondary antibody: biotin-goat anti-rabbit IgG (BA 1000; Vector Laboratories Inc.) then incubated in tertiary antibody (ABC elite; Vector Laboratories Inc.) and incubated in DAB+ Substrate (Dako, Carpinteria, Calif.) until brown color developed. Slides were counterstained in Haematoxylin, prior to dehydration and mounting. For IF, sections were incubated with an Alexa Fluor 488 goat anti-rabbit antibody (Invitrogen, Grand Island, N.Y.) and mounted in medium containing 4, 6-diamidino-2-phenylindole (DAPI; Vector Laboratories Inc.). All slides were viewed with an Olympus microscope and digital photographs were obtained using a constant exposure threshold. For active Caspase 3 and αSMA staining quantification, IMAGEJ® was used to measure the percent area of the image that contained positive staining. Proliferative index was calculated using IMAGEJ® (percentage of Ki67-positive nuclei/total nuclei).

Quantitative real-time PCR mRNA expression analysis was performed as previously described (Volk S W et al., Calcif Tissue Int 2014, 94:621-631). Briefly, RNA was extracted from fibroblasts, 4T1 cells, and mouse tissues (mammary fat pads and lungs from tumor naïve mice and tumors (14 days after orthotopic injection of 4T1 cells)), cDNA was generated, and Col1 and Col3 expression was compared to GAPDH as the endogenous control. For mouse tissues, lungs from young (16-18 weeks old) and aged (92-94 weeks old), and fat pads and tumors from young (10-24 weeks old) mice were used.

Fibroblast Isolation and Culture

Embryonic fibroblasts were harvested and genotyped as described previously (Volk S W et al., Cells Tissues Organs 2011, 194:25-37). Fibroblasts were cultured and passaged (≤passage 6) as described for 4T1 cells including the addition of L-ascorbic acid (A8960; Sigma) to the growth media to ensure secretion of a collagen-rich matrix.

Generation of Fibroblast-Derived Matrices

Decellularized matrices were generated as described (Beacham D A et al., Curr Protoc Cell Biol 2007, Chapter 10:Unit 10.9) using E18.5 embryonic fibroblasts. After 5-8 days in culture, the matrices were decellularized and were either stored in PBS at 4° C., or used immediately for experiments.

Proliferation Assays

Fibroblast-derived matrices were created in 96 well plates ($1.0 \times 10^4$ fibroblasts per well) as described above. 4T1 ($1.5 \times 10^4$) or MDA-MB-231 ($2.5 \times 10^4$) cells were plated and cultured on these decellularized matrices in growth media for 6 hours prior to changing to serum-free media overnight. Proliferation was measured using a BrdU, 96-well, ELISA-based assay (QIA58; EMD Millipore, Billerica, Mass.) using a Varioskan Flash plate reader (Thermo Fisher Scientific, Waltham, Mass.).

Analysis of Apoptotic Cells

4T1 or MDA-MB-231 cells ($1.0 \times 10^4$) were plated onto fibroblast-derived matrix-coated coverslips in 24 well plates, cultured in growth media for 16 hours, and then switched to serum-free media for 48 hours. After fixation with 4% paraformaldehyde, coverslips were incubated with an antibody directed against active Caspase 3 (ab2302; Abcam) and subsequently with an Alexa Fluor 488 donkey anti-rabbit antibody (Invitrogen), prior to mounting in medium containing DAPI. Fluorescence was viewed as described above for sections.

Adhesion Assays

For assessment of Col3 modulation of 4T1 morphology and adhesion, fibroblasts ($5.0 \times 10^4$) were plated and cultured in 24-well plates for 48 hours in growth media prior to subsequent seeding of 4T1-GFP cells ($8.0 \times 10^5$). 4T1-GFP cells were allowed to adhere for 2 hours in growth media or remain in culture for 48 hours in serum-free media to assess morphology, then fixed and imaged. For adhesion, GFP intensity was quantitated using IMAGEJ®. For adhesion in collagen-coated wells, 24-well plates were coated with 0.5 µg/cm² human placenta-derived (hP) collagens hPCol1 (354243; BD Biosciences), hPCol3 (354244; BD Biosciences), or a 50:50 by weight (0.5 µg/cm² total collagen) or 100:50 by weight (0.75 µg/cm² total collagen) mixture of both. 4T1 cells ($5.0 \times 10^5$) were plated in growth media and allowed to adhere for 2 hours. Attached cells were stained with crystal violet, and OD 570 was measured using a Varioskan plate reader. For adhesion to a substratum with stiffness similar to mammary fat pad (Otranto M et al., Cell Adh Migr 2012, 6:203-219), hydrogels (6 kPa) were generated as described previously (Olsen A L et al., Am J Physiol Gastrointest Liver Physiol 2011, 301:G110-8) on 12 mm coverslips in 24-well plates. The hydrogels were coated with hPCol1 and hPCol3 at 0.03 mg/ml or a 50:50 by weight mixture of both. 4T1-GFP cells were allowed to attach as described above, and GFP intensity (509 nm) was read in a Varioskan plate reader. Data between separate experiments was normalized to gels coated with rat tail collagen (354236; BD Biosciences). For MDA-MB-231 adhesion in collagen-coated wells, MDA-MB-231 cells ($2.5 \times 10^5$) were plated in growth media and allowed to adhere for 1 hour, and analyzed as above for 4T1 cells.

Invasion and Migration Assays

Migration was assessed in 24-well trans-well plates (353097; BD Biosciences) that were coated with 1 µg/cm² recombinant human (rh) Col1(354254; BD Biosciences), rhCol3 (354255; BD Biosciences), or a 50:50 by weight mixture of both. $5.0 \times 10^5$ 4T1 or MDA-MB-231 cells were plated in the upper chambers in serum-free media and allowed to migrate for 20 hours (lower chamber contained growth media). Cells collected from the bottom of the porous membrane were stained with crystal violet, which was quantitated as above. Invasion was assessed similarly except that the collagens were added to MATRIGEL® (354230; BD Biosciences) used to coat the top of the membranes before cell seeding. Cancer cells that invaded through the collagen-supplemented simulated-basement membrane were quantitated as described above. For MDA-MB-231 invasion and migration, hPCol1, hPCol3, or a 50:50 by weight mixture of both was used.

Second Harmonic Generation and Collagen Fiber Analysis

Imaging of fibrillar collagen was performed on a Leica SP5 confocal/multiphoton microscope by tuning the Coherent Chameleon Ultra II Ti: Sapphire laser to 800 nm and collecting second harmonic (SHG) signal on a non-descanned detector (NDD) configured to capture wavelengths below 495 nm. To distinguish true SHG signal from autofluorescence, fluorescence images at wavelengths of 495-560 nm (green autofluorescence) and 560-620 nm (red autofluorescense) were simultaneously acquired on two additional NDDs and subtracted from the original SHG image. Collagen signal and orientation was analyzed as described previously (Tang S Y et al., Circulation 2014, 129:1761-1769), with few modifications. IMAGEJ® was used to calculate the percent of the images that contained SHG-positive pixels, as a measure of collagen fiber intensity. IMAGEJ® was then used to generate a fast Fourier transform (FFT) powerplot of the fibrillar collagen signal. An ellipse was superimposed over the positive signal, and the major and minor axes of the ellipse were measured. An aspect ratio (major/minor axis) with a smaller value indicated random orientation, and larger values indicated orientated, aligned collagen fibers. For Tumor Associated Collagen Signature (TACS) quantification, fibers at the tumor boundary were analyzed using CurvAlign software (http://loci.wisc.edulsoftwarelcurvealign). The sum of all collagen fibers with angles between 0-30 degrees from the tumor boundary were considered to be TACS-2 and fibers with angles between 60-90 degrees classified as TACS-3, as previously described (Zhang K et al., Nat Cell Biol 2013, 15:677-687).

Data Analysis

Values are expressed as means±standard deviation (SD), unless otherwise stated. A one-tailed Fisher's exact test was performed to compare spontaneous tumor incidence between Col3+/+ and +/− mice. For in vivo experiments, unpaired student's t-tests were used to determine the significance of differences between mouse genotypes. For in vitro analyses, paired t-tests were utilized to compare fibroblasts from littermate embryos that were isolated, cultured, frozen, and passaged together, and 1-way ANOVAs followed by Tukey-posthoc tests were used to compare cancer cell properties on different collagens. Study groups were compared utilizing GraphPad Prism 5 statistical software. P-values <0.05 were considered statistically significant.

Results

Col3 Haploinsufficiency Promotes Development of Spontaneous Neoplasia

Spontaneous tumors have been shown to develop more frequently in aged (>1 year) female Col3+/− mice compared to age- and sex-matched wild-type littermates [12/73 (16.4%) Col3+/− mice versus 3/58 (5.2%) Col3+/+ mice; P<0.05]. Histopathology confirmed the diagnosis of neoplasia in all masses on which a biopsy was performed (13 masses total) (Table 1). Although a variety of tumor types were represented, mammary carcinoma was found in two Col3+/− mice (FIGS. 9A-9F). Given the increased incidence of spontaneous tumor development in Col3+/− mice and the potential role of Col3 in suppressing aggressive breast cancer behavior in women, a study to examine mammary tumor growth and metastasis in Col3-deficient mice, using the syngeneic 4T1 model of breast cancer was conducted (Miller F R et al., Invasion Metastasis 1983, 3:22-31).

TABLE 1

Spontaneous tumor development in Col3+/+ and Col3+/− mice

| Col3+/+ (in 58 mice >1 year old) | Col3+/− (in 73 mice >1 year old) |
| --- | --- |
| Histiocytic sarcoma | Mammary carcinoma (2) |
| Pulmonary carcinoma | Squamous cell carcinoma (forestomach) |
|  | Hepatocellular carcinoma |
|  | Histiocytic sarcoma |
|  | Adrenocortical carcinoma |
|  | Pulmonary adenoma |
|  | Spindle cell sarcoma |
|  | Poorly-differentiated sarcoma (hindlimb) |
|  | Lymphosarcoma (2) |

Col3 Haploinsufficiency Promotes Primary Tumor Growth and Metastasis

Liu et al. previously generated Col3−/− mice by homologous recombination, replacing the promoter and the first exon of the Col3a1 gene with a neomycin cassette (Liu X et al., Proc Natl Acad Sci USA 1997, 94:1852-1856). Since these global knockout mice, rarely survive beyond the perinatal period (Liu X et al., Proc Natl Acad Sci USA 1997, 94:1852-1856), Col3-haploinsufficient mice were used to study Col3's effects on mammary tumor development. These mice have been confirmed to express ≤50% Col3 in all tissues examined to date (Liu X et al., Proc Natl Acad Sci USA 1997, 94:1852-1856; Volk S W et al., Calcif Tissue Int 2014, 94:621-63126; Stevenson K et al., Mol Cell Biochem 2006, 283:107-114; Briest W et al., J Pharmacol Exp Ther 2011, 337:621-627). Fibrillar collagens, including Col3, are extracellular matrix components of normal human and rodent mammary tissue (Deak S B et al., Matrix 1991, 11:252-258; Mori S et al., Int J Biol Sci 2014, 10:825-833). Immunohistochemical localization of Col3 within the skin and underlying subcutaneous fat including mammary tissue in Col3+/+ mice revealed robust Col3 staining surrounding blood vessels and within the dermis, periadipocyte matrix and the intralobular stroma of mammary ducts (FIGS. 1A-1F). By comparison, Col3 immunostaining appeared less pronounced in sections from tissues harvested from Col3+/− mice. Quantitative RT-PCR confirmed a significant reduction in Col3 expression in the mammary fat pad of young adult Col3+/− mice compared to wild-type littermates (p<0.05).

Figures 1A, 1B, 1C, 1D, 1E, 1F:
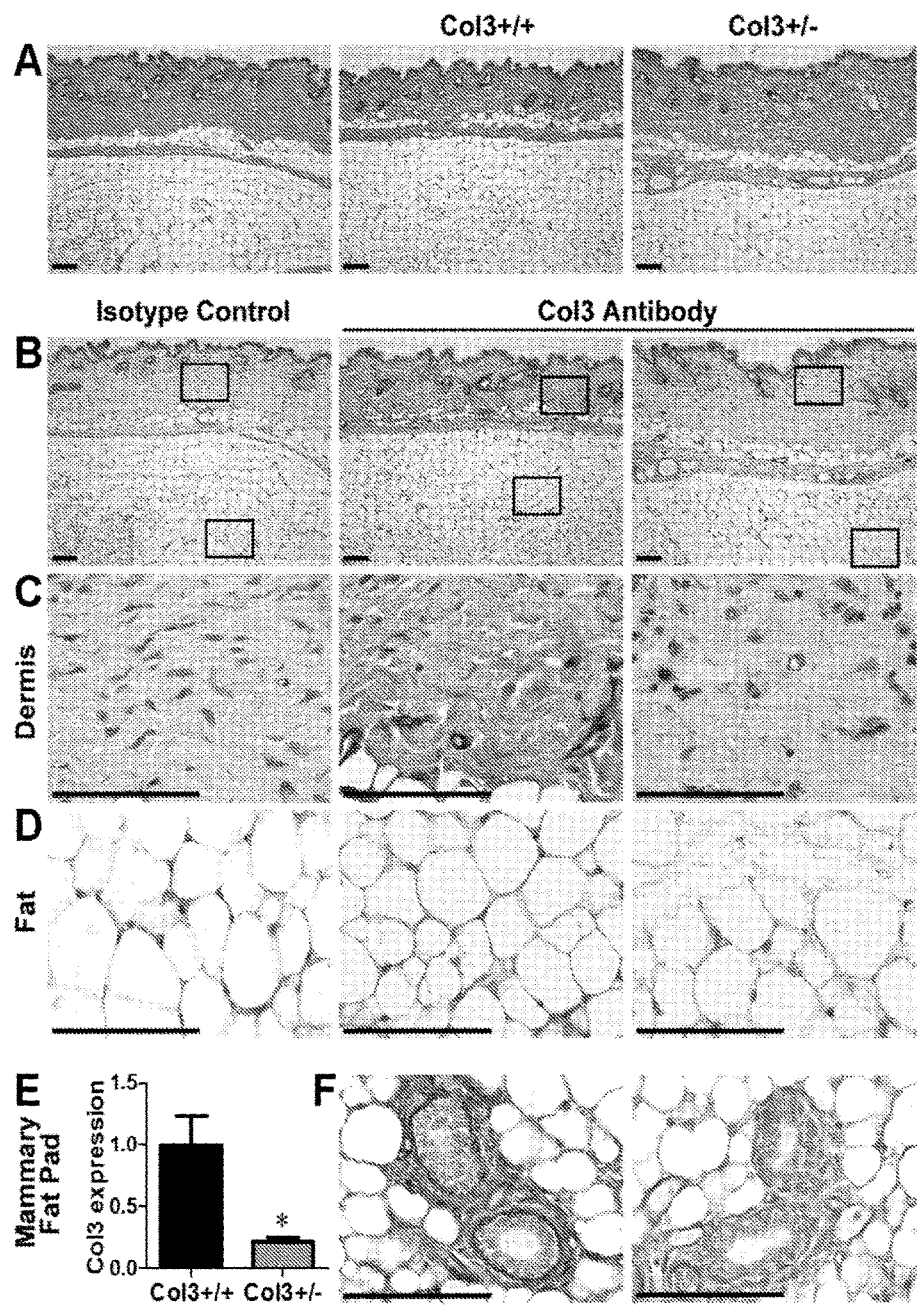
FIGS. 1A-1F illustrate reduced levels of Col3 in Col3+/− mouse skin, subcutaneous fat and mammary tissue compared to that found in these structures in normal (wild-type, Col3+/+) mice.
Figure 2A:
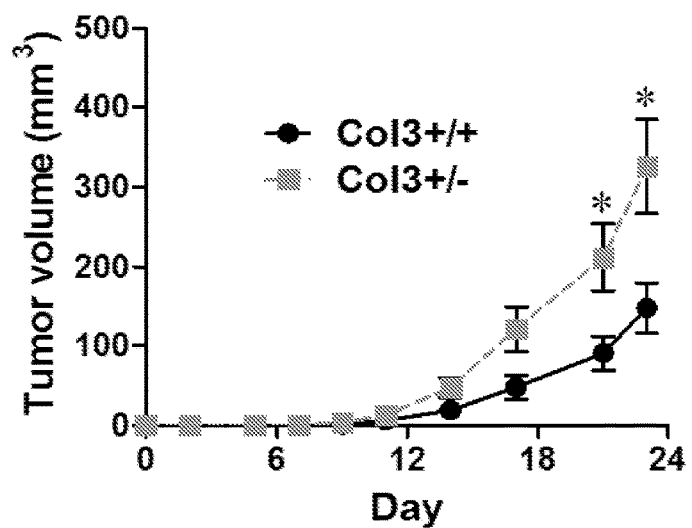
Figure 2B:
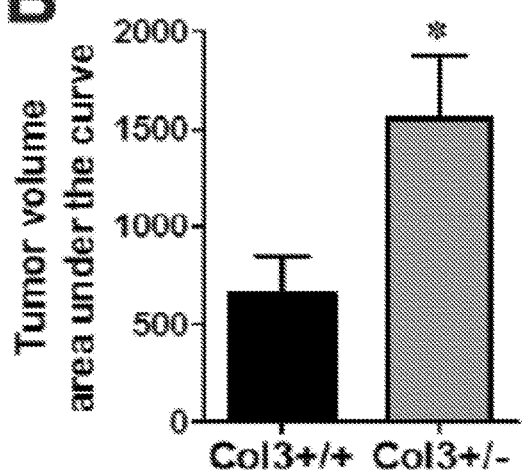
Figure 2C:
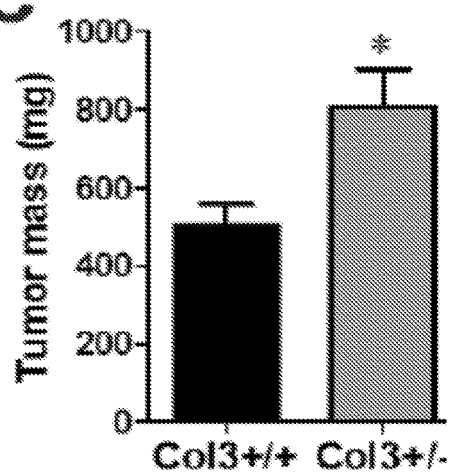

To determine whether diminished levels of Col3 drive aggressive tumor behaviors, 4T1 cells were injected orthotopically in Col3 wild-type and haploinsufficient littermates and primary tumor growth and metastasis were assessed. Primary tumor size was measured every 2-3 days following injection of 4T1 cells into either Col3+/+ or +/− mice. By day 21, primary tumors in Col3+/− mice were twice as large as tumors in Col3+/+ mice (FIG. 2A; p<0.05). Both the cumulative effect of Col3 deficiency on 4T1 tumor growth, analyzed by measuring the area under the curve for each tumor (Duan F et al., J Immunol Methods 2012, 382:224-228) and the tumor mass at the study end-point (day 24) (FIGS. 2B-2C), confirmed that tumor growth is significantly (*p<0.05) increased by Col3 deficiency.

Figure 2H:
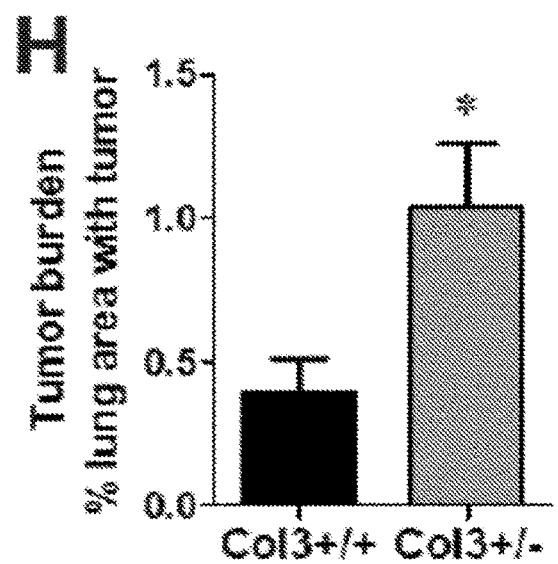

Because mortality in breast cancer patients is almost always associated with metastases rather than the primary tumor, Col3-deficiency was assessed to determine whether it also increased pulmonary metastasis in the 4T1 breast cancer model (FIGS. 2D-2H). Quantitative analysis revealed a nearly 3-fold increase in gross metastases in Col3+/− compared to Col3+/+ lungs (*p<0.05; FIG. 2F). Quantitative histologic assessment of H&E-stained lung sections confirmed that both the number of metastatic nodules and the tumor burden (% total lung area) were significantly greater in Col3+/− mice compared to Col3+/+ littermates (FIGS. 2G and 2H; *p<0.05).

Figure 3:
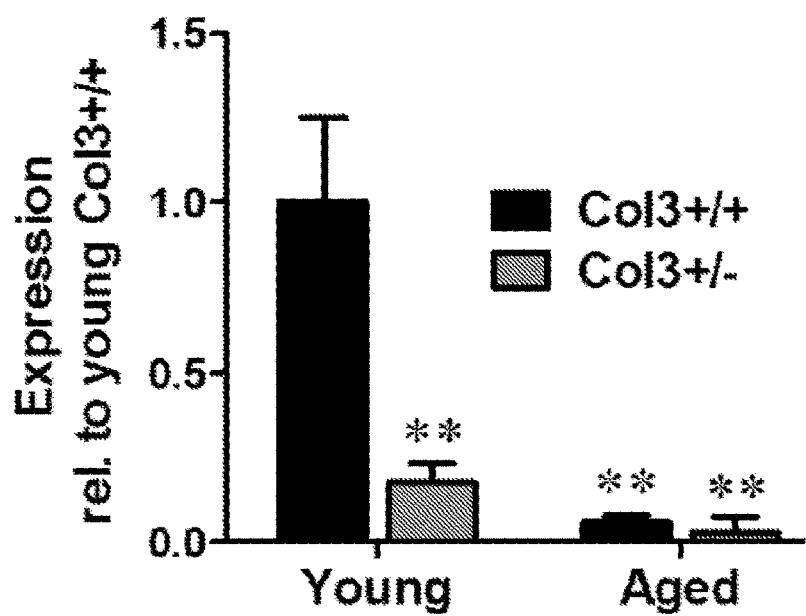
FIG. 3 illustrates Col3 expression in lungs from young (n=4 Col3+/+ and n=6 Col3+/−) and aged (n=3 Col3+/+ and n=3 Col3+/−) mice relative to young Col3+/+ lungs. The graph shows that Col3 is reduced in the lungs of Col3+/− mice relative to Col3+/+ mice and that age dramatically diminishes Col3 expression. Data represent means±SEMs, **p<0.01.

Next, an investigation was conducted to determine whether age impacts Col3 expression in the pre-metastatic niche (lung) of Col3+/− mice. Collagen, including Col3, is a normal component of the lung with Col3 expression attributed to pulmonary fibroblasts in several studies (Parra E R, Clinics (Sao Paulo) 2010, 65:425-432; Kelley J et al., Lung 1989, 167:313-322; Hance A J et al., J Clin Invest 1976, 57:102-111). As anticipated in this global knockout Col3 strain, pulmonary Col3 was significantly reduced in Col3+/− mice compared to Col3+/+ littermates (FIG. 3; **p<0.01). As suggested by previous studies examining the effect of age on Col3 expression in tissues (Volk S W et al., Calcif Tissue Int 2014, 94:621-631; Parra E R et al., Clinics (Sao Paulo) 2010, 65:425-432; Takeda K et al., J Cell Physiol 1992, 153:450-459; Varani J et al., Am J Pathol 2006, 168:1861-1868; Mays P K et al., Mech Ageing Dev 1988, 45:203-212; Benatti B B et al., Connect Tissue Res 2008, 49:401-408), advanced age (>23 months) is associated with a dramatic reduction in pulmonary Col3 expression (p<0.01). In addition to advancing age, smoking, the postmenopausal state and medications (such as steroids and Histone Deacetylase inhibitors) can preferentially decrease Col3 compared to Col1 and decrease Col3 levels to that found in our Col3+/− mice. These data highlight the clinical relevance of Col3 loss in tissues that may be colonized by cancerous cells and a large population of individuals that may benefit from this technology of Col3-directed therapies.

Figures 4A, 4B, 4C, 4D, 4E, 4F:
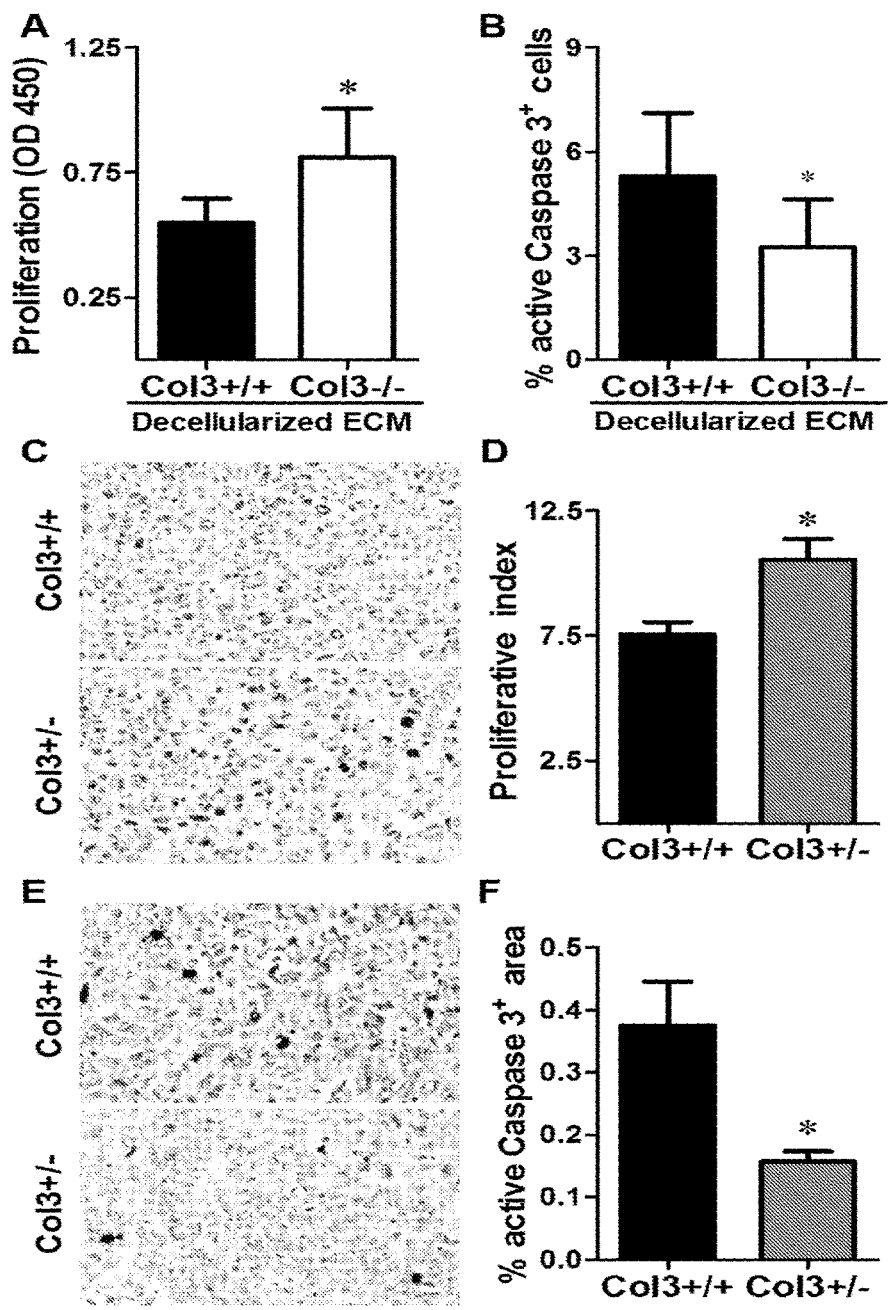
FIGS. 4A-4F illustrate the finding that a Col3-deficient microenvironment promotes breast cancer cell proliferation and inhibits cell death.

Col3 Deficiency Promotes Proliferation and Inhibits Apoptosis of Breast Cancer Cells Without being bound by theory, an increase in proliferation, a decrease in apoptosis or both, were hypothesized to mediate the accelerated primary tumor growth seen in Col3+/− mice. To differentiate between these possibilities, BrdU incorporation and active Caspase 3 activity was examined in 4T1 cells cultured on wild-type and Col3-deficient cell-derived matrices in vitro. Col3-deficient decellularized matrices were prepared from Col3−/− embryonic fibroblasts, as culture and passage could potentially induce variations in Col3 production by Col3+/− fibroblasts. Increased BrdU incorporation was observed in 4T1 cells cultured on Col3−/− fibroblast-derived matrices, relative to that seen with cells cultured on Col3+/+ fibroblasts derived-matrices (*p<0.05; FIG. 4A). In addition, there was a significant decrease in active Caspase 3 staining in 4T1 cells cultured on matrices lacking Col3 (Col3−/−) following serum-deprivation (*p<0.05; FIG. 4B). Consistent with these in vitro findings, tumor cell proliferation was significantly increased and apoptosis significantly decreased in 4T1 tumors grown in Col3+/− mice compared to Col3+/+ littermates, as evidenced by Ki67 and active Caspase 3 staining respectively (*p<0.05; FIGS. 4C-4F). Thus, both mechanisms—increased proliferation and decreased apoptosis—contribute to increased primary tumor growth in Col3+/− mice compared to wild-type littermates.

Col3 Deficiency Promotes a Metastatic Phenotype in vitro

Figure 5A:
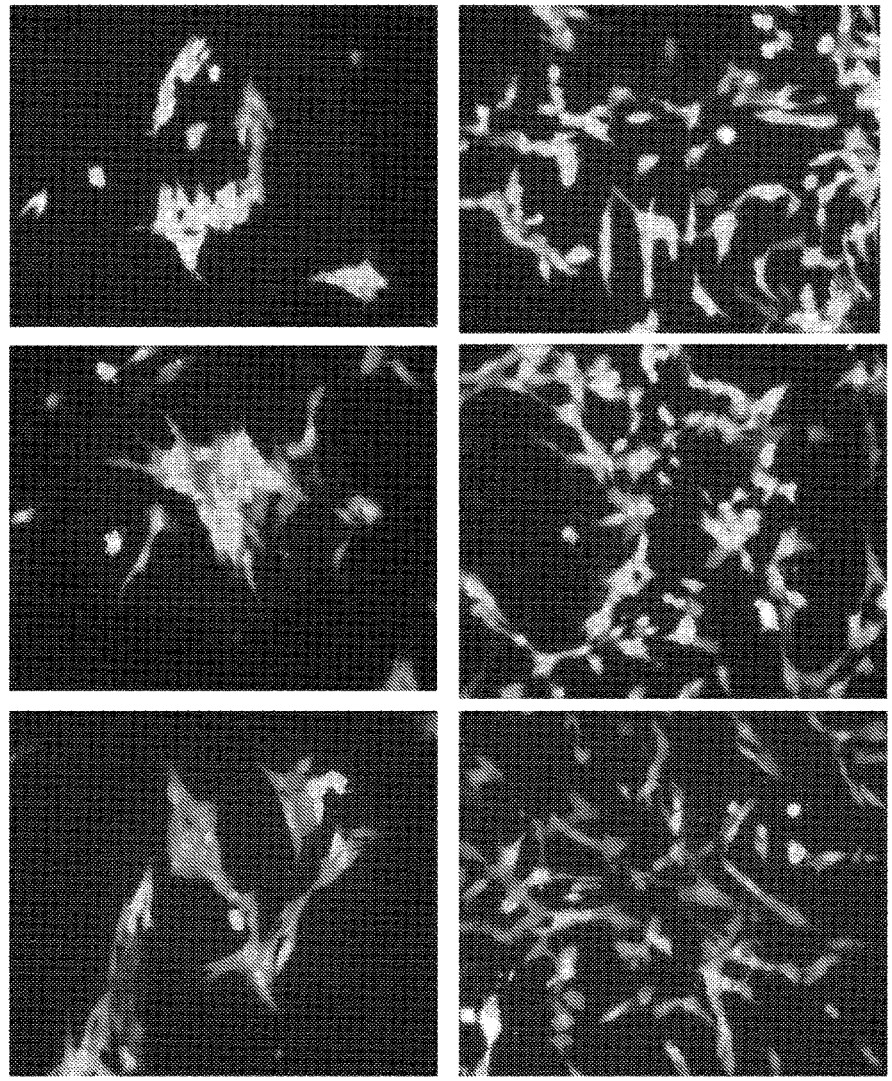
FIGS. 5A-5E illustrate the finding that 4T1 tumor cell morphology is changed and adhesion is enhanced in Col3-deficient microenvironments.
Figure 5B:
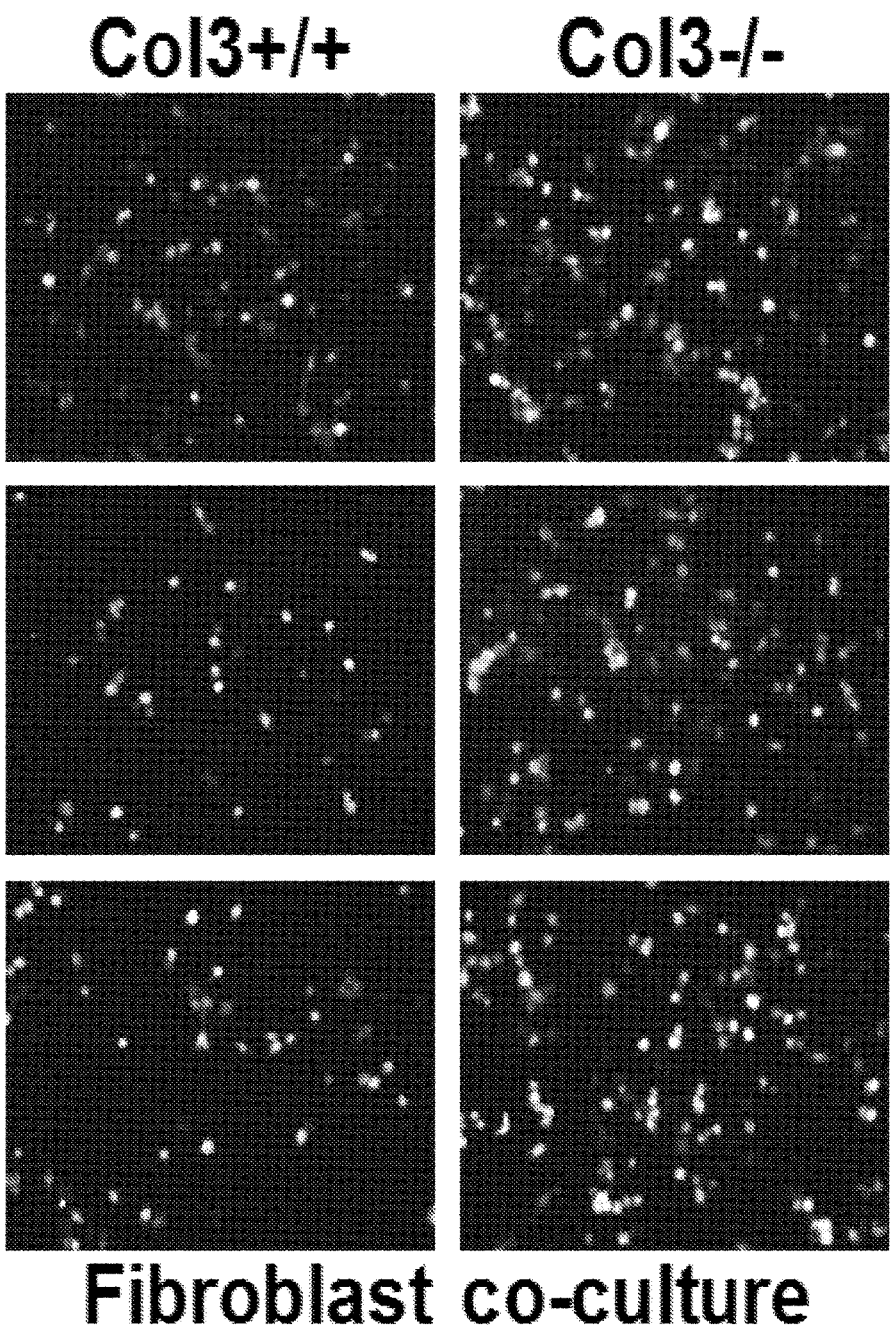
Figures 5C, 5D, 5E:
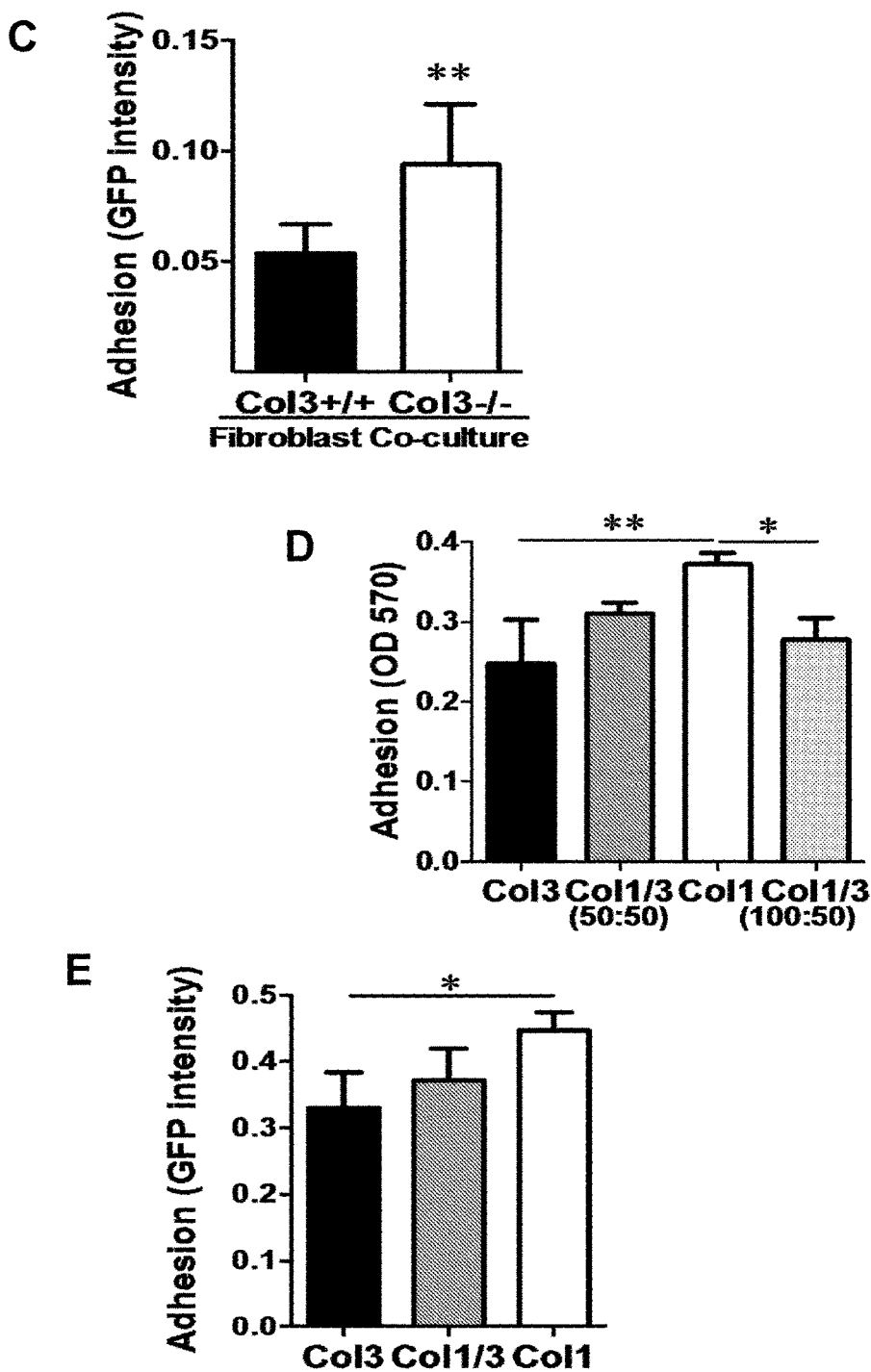

In order to mimic the effects of the tumor stroma in an in vitro system, 4T1 cells were co-cultured with wild-type and Col3−/− fibroblasts. A marked increase in 4T1 cell numbers in the presence of Col3−/− fibroblasts was observed (FIG. 5A). In addition, a striking difference in 4T1 cell morphology (FIG. 5A) was observed. Consistent with cell morphology on tissue culture plastic, 4T1-GFP cells co-cultured with wild-type (Col3+/+) fibroblasts grew as aggregates. In contrast, when co-cultured with Col3−/− fibroblasts, cells dispersed throughout the culture (FIG. 5A). Adhesion assays demonstrated that the number of adherent 4T1 cells was significantly increased when plated onto Col3−/− fibroblasts compared to Col3+/+ fibroblasts (FIGS. 5B-5C; p<0.01), suggesting that this dispersed phenotype may be due to Col3-dependent alterations in cell adhesion. To determine whether Col3 directly affects adhesion or whether this effect is instead mediated by modulation of fibroblast phenotype, 4T1 cells were plated in wells coated with Col3, mixtures of Col1/3, or Col1. Even in the absence of fibroblasts, 4T1 adhesion was decreased on a Col3 substrate compared to Col1 substrate alone (FIG. 5D; p<0.01). Adhesion of 4T1 cells on a mixture of the two collagens (50:50 by weight, total collagen constant) was intermediate between either collagen alone. To ensure that the decreased adhesion of 4T1 cells was due to an increase in Col3 rather than loss of Col1, 4T1 adhesion was also examined on a collagen substrate of constant Col1 and additional Col3 (Col1/3 100:50 by weight). Even with an increase in total collagen, the addition of Col3 significantly reduced 4T1 adhesion (*p<0.05). The stiffness of the tumor microenvironment can affect cell adhesion (Jaalouk D E et al., Nat Rev Mol Cell Biol 2009, 10:63-73). Adhesion of 4T1 cells to the fibrillar collagens (Col1, Col3 or Col1/3 50:50 by weight mixture) on hydrogels of physiologically relevant stiffness was compared (6 kPa, Otranto M et al., Cell Adh Migr 2012, 6:203-219), which are significantly softer than tissue culture plastic. 4T1 cell adhesion to Col3, Col1/3, and Col1-coated hydrogels again confirmed that Col3 significantly reduced the number of attached 4T1 cells (FIG. 5E; *p<0.05). Thus, on a matrix of biologically relevant stiffness, Col3 directly reduced breast cancer adhesion. Adhesion of human MDA-MB-231 cells was also significantly decreased on Col3 compared to Col1 (FIG. 10A), thus supporting a shared response to Col3 by triple negative breast cancer cells in mice and humans.

Figures 6A, 6B, 6C, 6D:
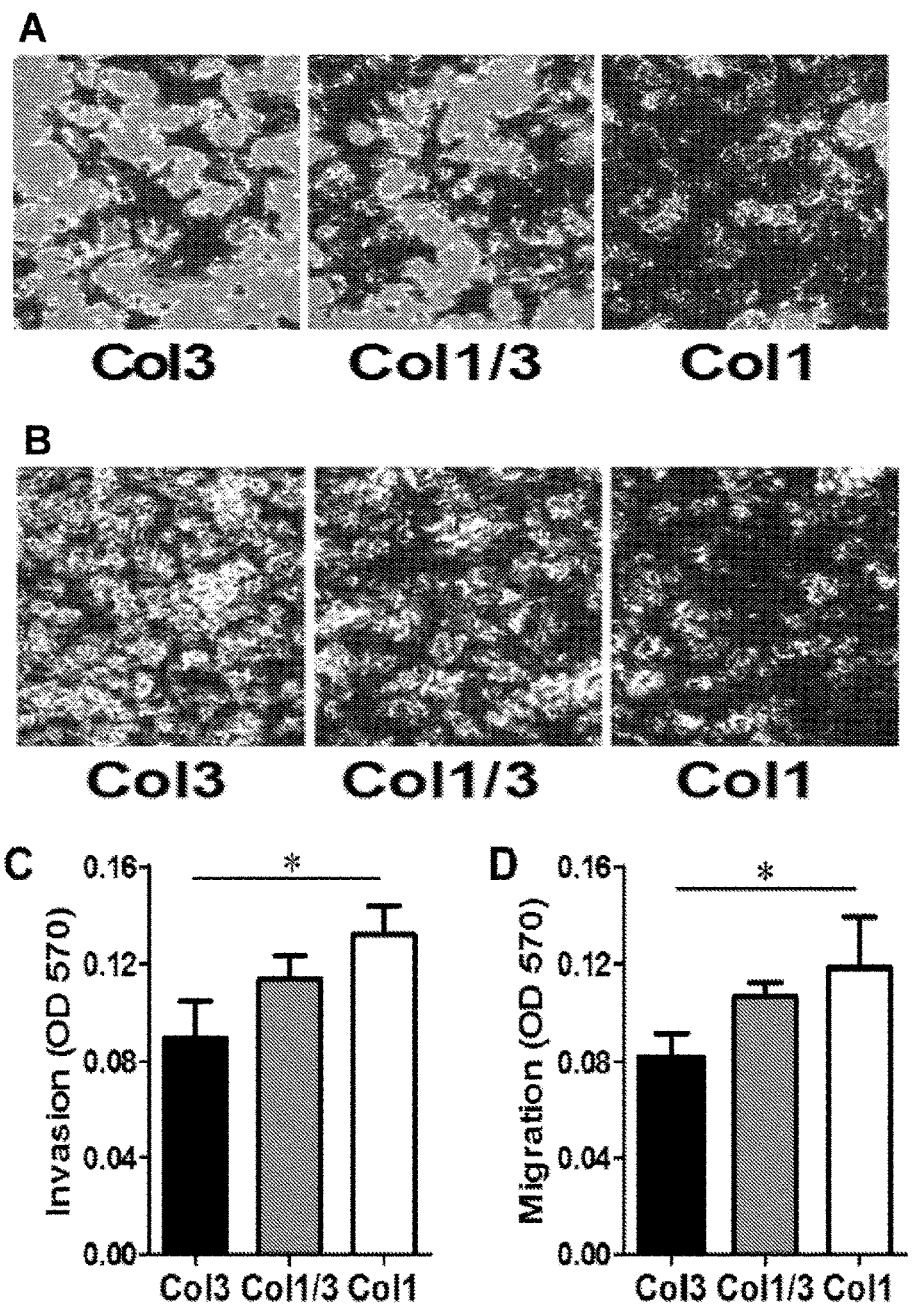
FIGS. 6A-6D illustrate the finding that Col3 impairs tumor cell invasion and migration.

Given the increased incidence of metastasis associated with Col3 haploinsufficiency in the 4T1 model of murine breast cancer, the ability of Col3 to modulate invasion and migration of breast cancer cells through basement membrane gels supplemented with Col3, a 50:50 by weight mixture of Col1 and Col3, or Col1 alone using standard in vitro trans-well assays was examined. Invasion of 4T1 or MDA-MB-231 cells was significantly inhibited in Col3-containing gels compared to gels with Col1 alone (FIGS. 6A, 6C, and 10B; *p<0.05). Similarly, the presence of Col3 resulted in a significant reduction in 4T1 and MDA-MB-231 cell migration (FIGS. 6B, 6D, and 10E; *p<0.05). Thus, Col3 directly limits murine and human breast cancer cell invasion and migration, supporting the hypothesis that Col3 suppresses metastatic escape at the level of the primary tumor.

Figures 7A, 7B, 7C, 7D:
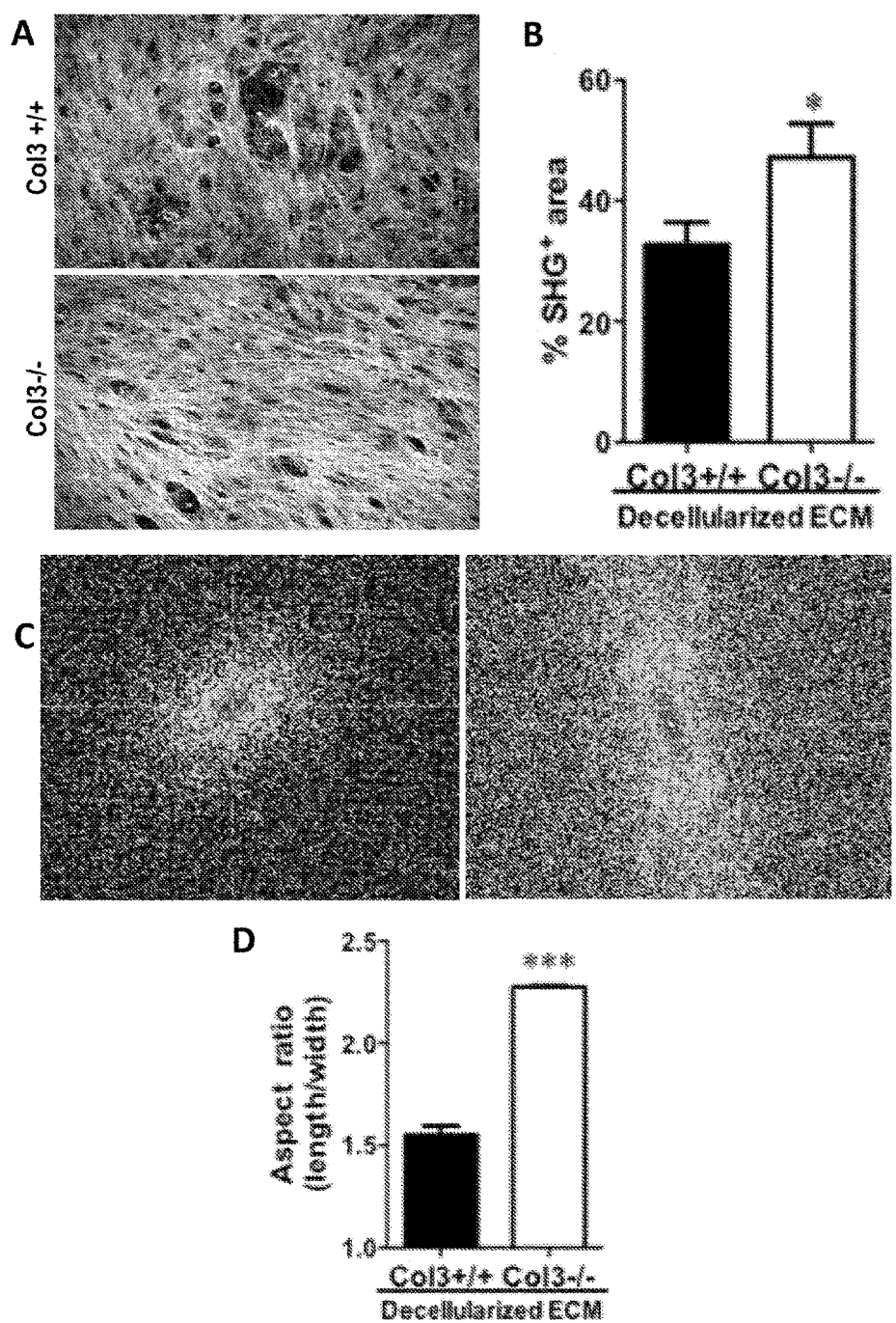

Col3 Deficiency Promotes a Pro-carcinogenic Stroma by Regulating Collagen and Myofibroblast Density and Alignment While Col3 can directly suppress a metastatic phenotype (adhesion, migration and invasion) in 4T1 (FIGS. 5A-E and FIGS. 6A-D) and human (MDA-MB-231) breast cancer cells (FIGS. 10A-C) in vitro, Col3 loss in the TME also had significant effects on myofibroblast induction (FIG. 7G-I) and collagen density and alignment (FIGS. 7A-F and FIGS. 11A-C) that may indirectly regulate tumor cell behavior. Collagen reorganization is increasingly recognized as a key determinant of a pro-carcinogenic microenvironment, with increasing collagen alignment facilitating metastasis. Compared to a complex or disorganized matrix, aligned collagen provides a directed pathway for tumor cells to migrate on and invade surrounding tissues. To determine whether Col3 potentially regulates fibrillar collagen production and organization in the tumor stroma, collagen SHG imaging of fibroblast-derived matrices (FIG. 7A) was conducted. It was discovered that Col3−/− fibroblasts produced a more highly aligned and fibrillar matrix than wild-type cells (FIGS. 7B-7D; *p<0.05 and *p<0.001). To confirm that Col3 regulates stromal density and organization of breast cancer in vivo, 4T1 tumors were harvested from mice after 14 days. The H&E stained tumor sections showed no obvious differences in general tumor morphology between genotypes (FIG. 7E). However, when sections were imaged using SHG (FIG. 7F), as with the fibroblast-derived matrices, the tumors from Col3-deficient (Col3+/−) mice contained more mature and aligned collagen fibers than the Col3+/+ tumors, similar to that seen with the fibroblast-derived matrices. Furthermore, at the tumor periphery, collagen fibers exhibited a more invasive phenotype characterized by alignment perpendicular to the tumor border in Col3+/− mice compared to that seen in Col3+/+ mice. Stromal collagen density and organization at the tumor boundary can be characterized using SHG to generate tumor associated collagen signature (TACS) scores. The invasive TACS-3 has been shown to correlate with aggressive behavior in murine breast cancer models and has been established as an independent prognostic indicator in women regardless of tumor subtype, grade and size, hormone receptor status, and lymph node status. TACS analysis confirmed a significant decrease in the non-invasive TACS-2 signature and a significant increase in the invasive TACS-3 signature in tumors of Col3 haploinsufficient mice compared to wild-type littermates (FIGS. 11A-11C; p<0.01 and *p<0.05, respectively). In summary, exogenous Col3, or strategies that increase tissue Col3 content, can reverse these aggressive collagen signatures in tumors (FIGS. 16A-16C).

Figures 7H, 7I:
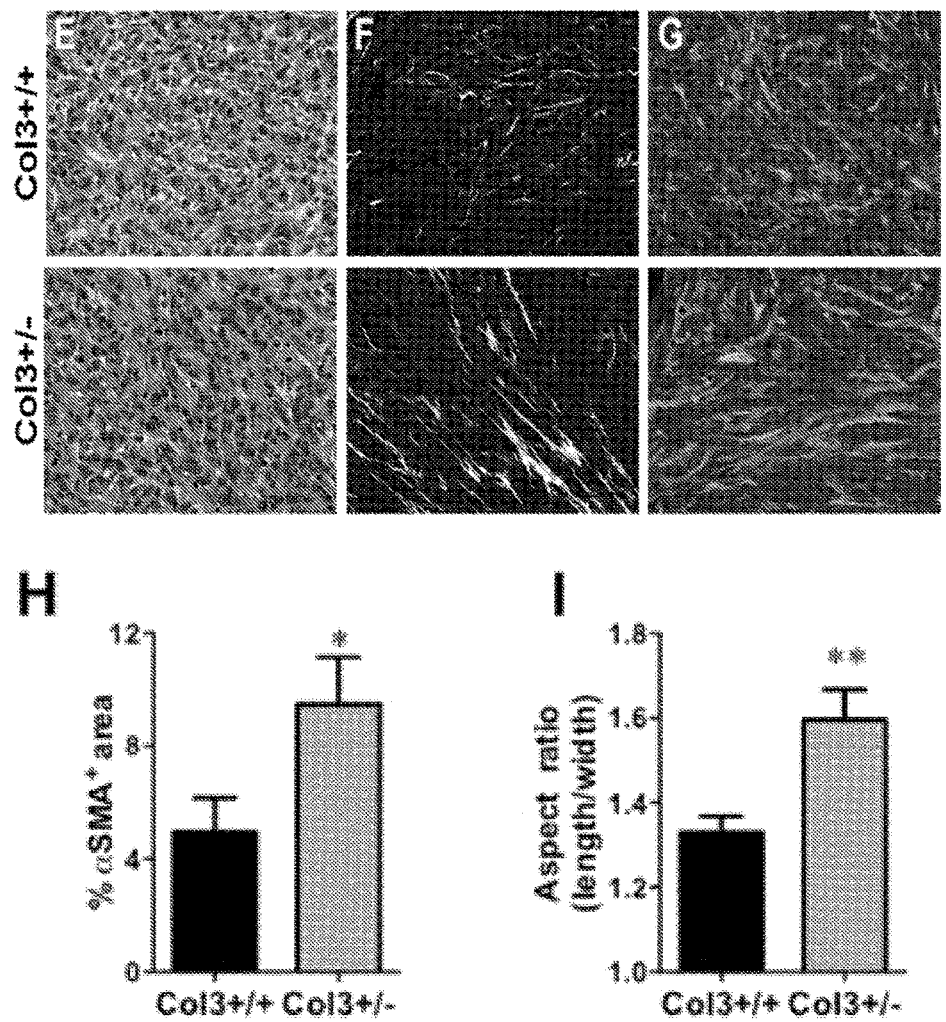
Figures 8A, 8B, 8C:
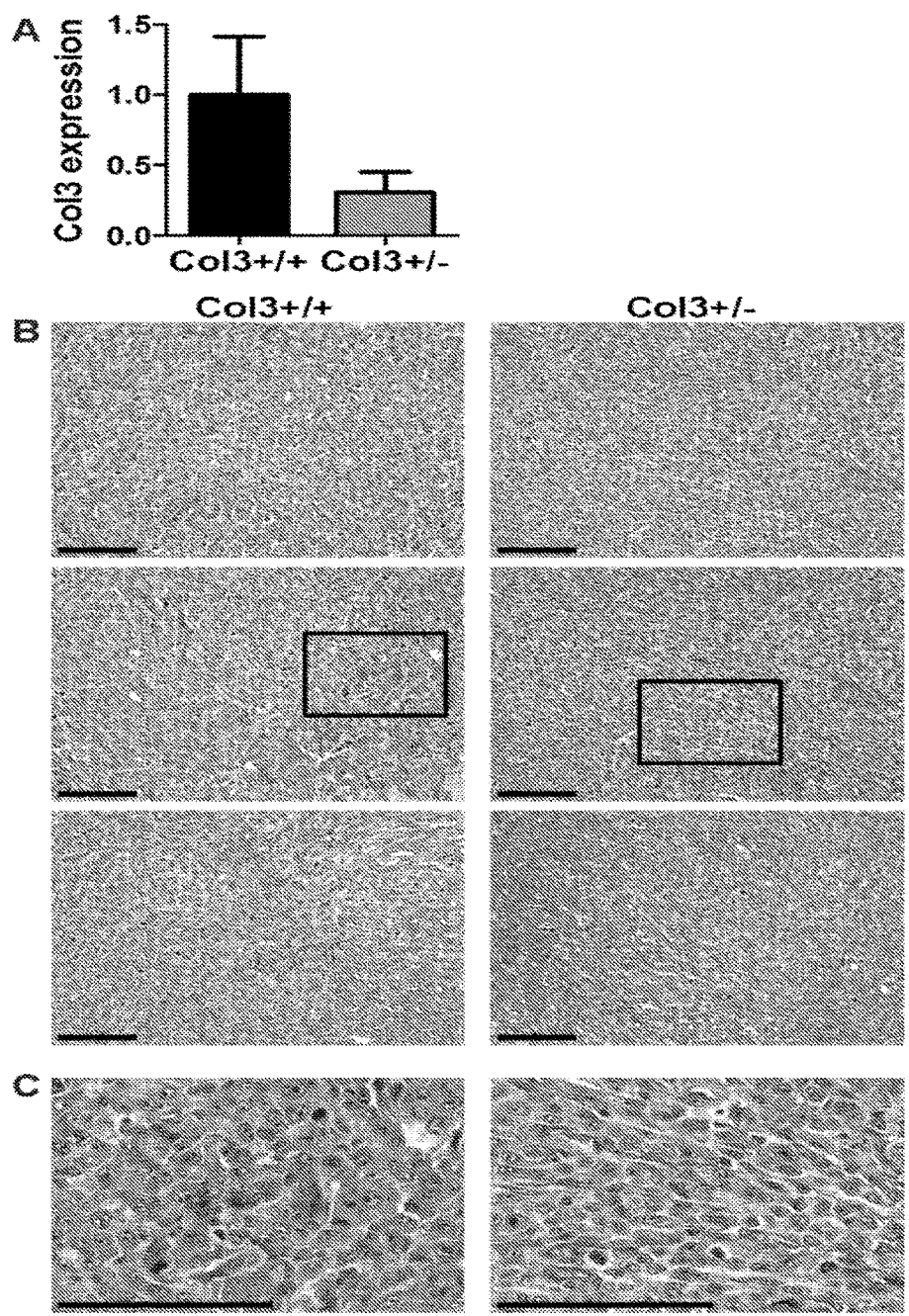
FIGS. 8A-8C illustrate that Col3 density is heterogeneous within 4T1 tumors.
Figures 9A, 9B, 9C, 9D, 9E, 9F:
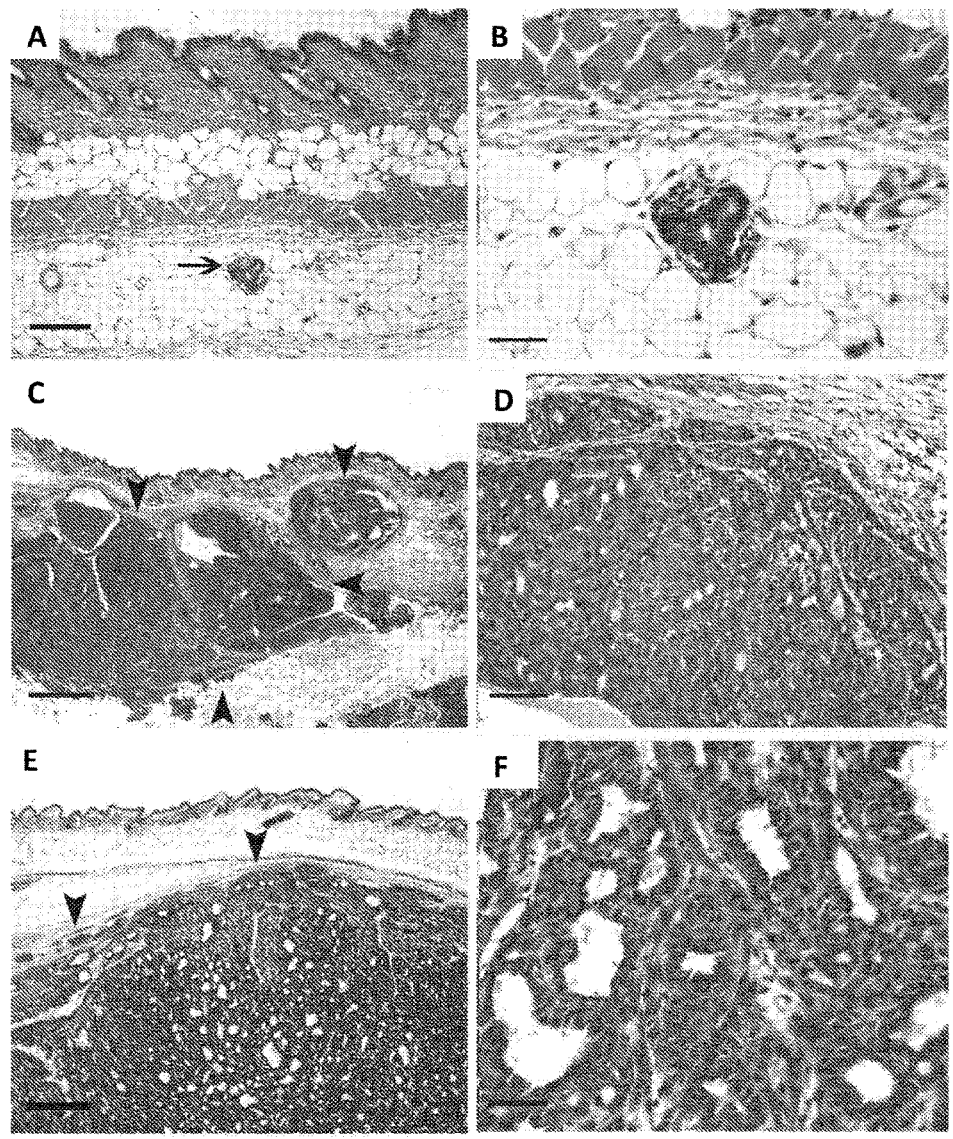
FIGS. 9A-9F illustrate the finding that Col3 deficiency leads to an increased incidence of spontaneous tumors, including mammary tumors, in aging mice.

In addition to the effects of Col3 on collagen density and alignment, the data presented herein demonstrate a role for Col3 in regulating myofibroblast fate and activity in the tumor microenvironment. Given the established role of myofibroblasts in inciting aggressive tumor phenotypes and the demonstration that Col3 deficiency promotes myofibroblast activity during wound healing, it was hypothesized that a Col3-deficient healing environment would exacerbate aggressive tumor behaviors following marginal excision of primary tumors. Col3+/− tumors were assessed to determine whether they contained more myofibroblasts than tumors in Col3+/+ mice. Based on expression of αSMA, a marker of myofibroblasts (FIGS. 7G-7H), it was discovered that tumors in Col3+/− mice had significantly increased stromal myofibroblast density (FIG. 7H; *p<0.05). CD31 immunofluorescence confirmed that the majority of αSMA-positive cells were not associated with vascular smooth muscle cells (data not shown). In addition, αSMA+ cells were organized in a striking, highly aligned pattern in the tumors of Col3+/− compared to Col3+/+ mice (confirmed by quantitative analysis in FIG. 7I; **p<0.01), suggesting that Col3 directs matrix organization or the ability of fibroblasts to interact with that matrix.

Figures 12A, 12B:
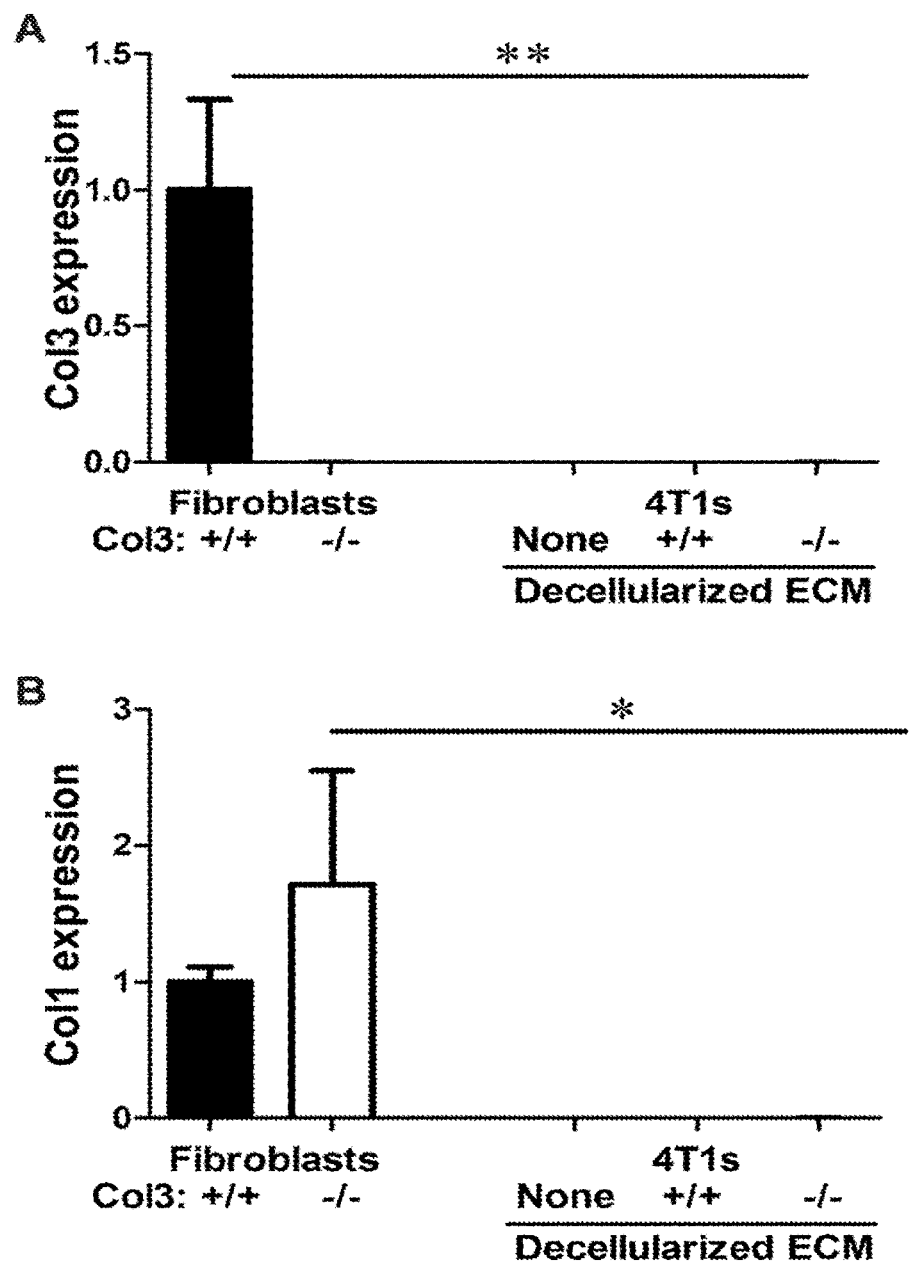
FIGS. 12A-12B illustrate the finding that 4T1 cells do not express Col1 or Col3 in culture when compared to embryonic fibroblasts, even when grown on matrices from Col3+/+ or Col3−/− fibroblasts. Col3 (FIG. 12A) and Col1 (FIG. 12B) mRNA expression in embryonic fibroblasts and 4T1 cells grown alone, or on decellularized matrix from Col3+/+ or −/− fibroblasts relative to Col3+/+ fibroblasts. For comparisons between cells:*, $p<0.05$; **, $p<0.01$ via 1-way ANOVA followed by Tukey post hoc test. Data represent means±SEMs.

To determine Col3 expression and localization within the stroma, immunohistochemistry of Col3 in tumors was performed 14 days following orthotopic injection. Although there was marked heterogeneity in the density of Col3 throughout the tumors of both Col3+/+ and Col3+/− mice (FIGS. 8A-8C), Col3 was found to be more aligned within tumors of Col3-haploinsufficient mice compared to wild-type littermates, similar to overall fibrillar collagen and myofibroblast organization, suggesting that Col3 deficiency early in the tumor environment alters collagen alignment at later stages. Production of Col1, Col3 or both was investigated in 4T1 cells. Compared to Col3+/+ fibroblasts, neither Col3 nor Col1 expression could be detected in cultured 4T1 cells, even when cultured on decellularized fibroblast matrices from either Col3+/+ or Col−/− fibroblasts (FIG. 12A-12B). Col3 expression in Col3−/− fibroblasts was not detectable. Consistent with increased fibrillar collagen production in the tumors of Col3+/− mice, there was a trend for increased Col1 expression in cultured Col3−/− compared to Col3+/+ fibroblasts. The lack of a more dramatic effect on Col1 levels suggest that the major effect of Col3 was on matrix organization, although temporal changes in Col1 may lead to significant changes at later times. Taken together, these data demonstrate that Col3 suppresses a tumor-inciting stroma and that a Col3-deficient microenvironment promotes breast cancer metastasis. The data presented herein also show that in response to a Col3 deficient tumor microenvironment, subsequent Col1 production by stromal cells in disproportionately increased compared to Col3 production over time (FIG. 21), which has important implications for controlling a tumor-permissive microenvironment.

Increasing Col3 in the Tumor Microenvironment Suppresses the Aggressive Phenotype of Both Murine and Human Breast Cancer Cells In Vivo To examine if exogenous Col3 would affect tumor cell properties in vivo, both 4T1 cells in our Col3 murine model and human triple-negative (TNBC) MDA-MB-231 breast cancer cells were orthotopically injected into immunocompromised NSG mice. When Col3 was added to 4T1 and MDA-MB-231 cells at the time of orthotopic injection in Col3+/+ (Balb/C) and NOD-Scid-Gamma (NSG) mice, respectively, growth of primary tumors was attenuated (FIG. 14A; 4T1 data shown).

Exogenous Col3 Reduces a Tumor-Permissive Microenvironment in Human MDA-MB-231 Tumors In Vivo Histology of MDA-MB-231 tumors showed that increasing local Col3 in the early TME dramatically changed tumor behavior. Compared to vehicle controls (FIG. 15A), tumors of cells mixed and injected with Col3 had a less aggressive phenotype (FIG. 15B), characterized by a decrease in collagen density and aggressive TACS (TACS-3) frequency (FIGS. 16A-E) and an increase in apoptosis within the tumor (FIGS. 14B and C). Thus, these data demonstrate that increasing Col3 locally can diminish aggressive behavior of human and murine TNBC cells in both Col3-sufficient and immunocompetent individuals.

In support of the fact that Col3 decreased mechanotransduction in tumor cells, addition of recombinant human Col3 to MDA-MB-231 cells at the time of orthotopic injection significantly diminished both total yes associated protein (YAP), a mechanosensitive marker, expression by ~50% and % nuclear phospho-YAP levels compared to controls (FIGS. 17A-C; *p<0.05). The ability of Col3 to modulate this pathway has significant implications, as both increased levels and nuclear translocation of YAP have been associated with breast cancer growth, metastasis and chemoresistance.

Furthermore, the data shows that addition of exogenous Col3 to MDA-MB-231 cells at the time of orthotopic injection can significantly reduce gelatinase activity in vivo by >30% (*p<0.05; FIG. 18A-C), suggesting matrix degradation and remodeling is reduced in the presence of Col3. Thus, increasing Col3 locally diminished aggressive behavior of human TNBC cells in both Col3-sufficient and immunocompetent individuals. Together, these in vitro and in vivo gain and loss of function studies support a role for Col3 in suppressing breast cancer growth, metastasis and local recurrence.

Col3 N-propeptide CR Domain Binds to and Alters the Activity of TGFβ

Like most other fibril-forming collagens, Col3 is synthesized from a precursor of carboxy-terminal and amino-terminal propeptides. The Col3 amino-propeptide contains a cysteine-rich (CR) domain which has high homology with other TGFβ-binding CR domains. TGFβ signaling, regulated in part by its bioavailability, is essential for the efficient conversion of fibroblasts into contractile myofibroblasts. It was suggested that tissue Col3 CR domain binds and sequesters TGFβ, thereby reducing its bioavailability. Biosensor data indicated that the Col3 CR domain binds TGFβ1 in a dose-dependent fashion (FIG. 19A). In addition, human breast cancer cells have diminished levels of the downstream TGFβ effectors, pSmad2 and 3, when cultured in the presence of human placental (hp)-derived Col3 (which contains the CR domain) compared to Col1 (FIG. 19B). Conversely, Col3−/− fibroblasts have significantly increased levels of pSmad2 compared to Col3+/+ fibroblasts (FIG. 19B). Finally, that addition of the CR domain peptide to Col3−/− fibroblast cultures attenuated TGFβ signaling (FIG. 19C). In addition to increased TGFβ-induced pSmads, data showed that levels of the profibrotic connective tissue growth factor (CTGF), a down-stream effector of TGFβ, were significantly increased in Col3-deficient fibroblasts in vitro and in 4T1 tumors of Col3+/− mice in vivo (FIGS. 19D-E; *p<0.05).

Col3 Regulates α11β1 Integrin Expression

Integrin α11β1 plays a critical role in myofibroblast differentiation and fibrosis. FIG. 20A provided the first evidence that Col3 suppressed α11 expression in fibroblasts. In addition to expressing more α11 integrin, Col3−/− fibroblasts appeared to be more efficient in all-clustering at focal adhesions compared to Col3+/+ fibroblasts (FIG. 20B), suggesting an increase in mechanosensing and/or transduction. Col3 suppressed α11 integrin expression, which may limit myofibroblast differentiation and mechanotransduction as well as play an important role in aggressive cancer behaviors (invasion and metastasis).

Col1/Col3 Ratio is Increased in 4T1 Tumors in Col3+/− Mice Compared to Col3+/+ Mice While fetal tissues have a low ratio of Col1/Col3, this ratio increases with age. The fibrosis/scar literature also suggests that the ratio may be a reliable clinical predictor of pathology. Since 4T1 tumors in Col3+/− mice were larger and more metastatic than those in Col3+/+ mice, the Col1/Col3 ratio over time in 4T1 tumors was measured (FIG. 21). While the Col1/Col3 ratio did not differ in tumors between genotypes during early tumor growth, by 23 days post orthotopic injection, the ratio was over 10× greater in Col3+/− mice comparted to controls, suggesting that decreased Col3 in the early tumor microenvironment can direct collagen production differentially over time.

Col3 Reduces Fibrillar Collagen Compaction and Alignment Modulation by Cells

Because collagen alignment is associated with matrix stiffening and mechanotransduction, the ability of Col3 to directly modulate matrix compaction and alignment has important clinical implications given the well-established role for mechanical regulation of breast cancer behavior including growth, metastasis and chemoresistance. Aggregates of fibroblasts and breast cancer (4T1) cells compacted and aligned fibrillar collagen less efficiently as the concentration of Col3 increases. In addition, cells migrated along the collagen fibers more readily when Col3 was absent (FIGS. 22A-22D).

Tumor Cells Attach and Interact with Electrospun Constructs

One goal for use of Col3 as a biomaterial is to electrospin Col3 with other components that form a biologically compatible scaffold. These electrospun composite scaffolds may comprise a biomimetic fraction (Col3) together with a slow-degrading Polycaprolactone (PCL) component that provides a structural backbone and a water-soluble, sacrificial poly(ethylene oxide) (PEO) that improves cell colonization and integration of the scaffold at the excision site, effectively localizing and stabilizing the Col3 factor and providing a provisional clinically applicable product. To begin creating and testing these constructs, collagen isolated from pepsin-treated bovine skin was coated onto electrospun PCL. 4T1 cells were plated onto the constructs, and visualized via scanning electronic microscopy (SEM) (FIGS. 23A-B). This data shows that cancer cells can interact with Col3 containing electrospun constructs and possess the potential to direct subsequent cell behaviors to control cancer growth and spread.

Col3 Promotes Tumor Cell Apoptosis in Human Breast and Lung Tumor Cell Lines

Col3 biomaterials may prevent regrowth by promoting apoptosis of tumor cells. To determine if Col3 affects apoptosis in human tumor cells, staurosporine, an agent with chemotherapeutic properties, was used to initiate apoptosis in vitro in MDA-MB-231 mammary and A549 lung tumor cell lines (FIGS. 24A-C). Cells were plated on recombinant-coated glass coverslips (FIG. 24A and FIG. 24C) or on collagen-coated PCL to determine if Col3 would affect apoptosis on an electrospun construct (FIG. 24B). Col3 significantly increased apoptosis in MDA-MB-231 cells compared to Col1-coated glass coverslips (FIG. 24A; *p<0.05). A similar trend was observed for these cells to apoptose more on Col3-coated PCL constructs compared to Col1 coated constructs (FIG. 24B) and for Col3 to promote apoptosis in human lung carcinoma A549 cells (FIG. 24C). Because staurosporin is known to possess chemotherapeutic properties, these data suggest Col3-directed therapies will potentiate chemotherapy effects and reduce tumor chemoresistance.

Determine the Role of Col3 in Limiting Cancer Cell Invasion and Migration via Regulation of Collagen Deposition and Remodeling To determine the impact of Col3 on malignant cell remodeling of the Col1 fibrous network, Col1/Col3 gels are generated at different physiologically-relevant ratios: 100/0, 90/10, 75/25, and 60/40, to a total collagen concentration of 3 mg/ml rhCol1 and rhCol3 (Fibrogen). Similar experiments are carried out using Col1 at a constant concentration, with Col3 added to achieve the ratios above. Notably, the gels are thick enough to avoid cell mechanosensing of the underlying culture dish. Cell aggregates of MDA-MB-231 cells (generated by hanging droplet culture) are plated on the gels and cultured for 6, 12, and 24 hours. Pairs of cell aggregates that are 100-400 μM away from each other (without other cells or aggregates in that range) are imaged and analyzed for SHG using a Leica TCS SP5 multiphoton system. The cell/aggregate outline is traced, as is the line between cells/aggregates, and the following is analyzed using ImageJ and Volocity platforms: a) collagen density along the inter-cell axis compared to other axes around the cell; b) the alignment of collagen fibrils relative to the inter-cell axis; and c) numbers of cells dispersed from the aggregate, along the inter-aggregate axis or otherwise. As controls, gels without cells are imagined and analyzed. The effects of Col3 on the structure of the Col1 fibrous network are visualized and quantified. The impact of Col3 on matrix remodeling-dependent cancer cell migration is determined.

To determine how the aberrant collagen composition, topography and biomechanics induced by Col3 loss direct spatiotemporal movement of breast cancer cells through the surrounding stroma, cell migration of three human TNBC cell lines (MDA-MB-231, -468, and BT-549; all in hand or commercially available from ATCC) are examined on decellularized matrix prepared from Col3+/+ and −/− fibroblast cultures, mimicking a native 3D matrix. Cells are labeled with CELLTRACKER™ Red dye (Life Technologies, Inc). Video microscopy is performed using a Leica inverted microscope fitted with an environmental control chamber over a 6 hour period (up to 12, if needed; 2 frames/minute). SHG imaging is at the conclusion of the experiment to determine the spatial orientation of cancer cells and the collagen matrix. Should simultaneous observation of collagen fibrils be deemed advantageous, the experiment can be repeated on the Leica multiphoton system to concurrently visualize the cells and image collagen using SHG. Migration and individual cell track data are analyzed.

Determine Whether Regional Col3 Loss in Human TNBC is Associated with Aggressive Stromal Signatures and Focal Invasion To determine if regional Col3 deficiencies impact breast cancer progression, the relationship between Col3 and collagen density and alignment in invasive and non-invasive regions is examined in human TNBC biopsy samples. The TNBC patient population are the subject for examination, due to the response of the two models of TNBC (4T1 and MDA-MB-231) to Col3, as well as the fact that this form of breast cancer is notoriously aggressive. Invasive and non-invasive regions are identified on H&E stained serial sections to ensure that the fields measured contain tumor stroma abutting malignant epithelium. SHG is used to quantitate invasive and non-invasive TACS. Col3 is detected by: 1) immunofluorescence, and 2) SHG in the forward and backward directions to detect Col1 and Col1+Col3-rich regions. In addition, SHG is used to quantify collagen density, alignment, fiber length and thickness using the CT-FIRE analysis (http://loci.wisc.edu/software/ctfire). α-smooth muscle actin+(α-SMA; a myofibroblast marker) CAF populations are quantified by immunofluorescence in invasive and non-invasive regions in serial sections of human TNBC biopsies (N=40). Both SHG and immunofluorescence images are captured on the same section, thus providing direct information regarding the spatial relationship of the remodeled collagen-rich ECM, Col3, TACS, and content and organization of the α-SMA$^+$ CAFs.

Determine if the Col3 CR Domain Modulates Myofibroblast Differentiation and Apoptosis in a TGFβ-Dependent Manner To determine if the CR peptide can modulate TGFβ signaling, low-passage (<5) embryonic (E18.5) Col3+/+ and Col3−/− fibroblasts are harvested and cultured in the presence and absence of 1.0 ng/ml TGFβ1, with and without CR peptide (0.025 and 0.05 μM) and three higher doses (0.25, 0.5 and 1.0 μM) or a control peptide (cysteine mutant). Levels of pSmad⅔, relative to total Smad, are determined by ELISA assay (Cell Signaling). As a positive control, TGFβ signaling is inhibited with either a well-characterized TGFβ-neutralizing antibody (R&D Systems) or the small molecule inhibitor SB-431542 (Sigma-Aldrich). All experiments are performed in triplicate using N=4 fibroblast pairs (Col3+/+ and Col3−/−) using the optimized CR dose that inhibits TGFβ signaling and the mutant CR peptide as a control.

To determine if the Col3 CR domain can attenuate myofibroblast differentiation induced by a Col3-deficient microenvironment, Col3 is added daily to cultures of Col3−/− fibroblasts undergoing myofibroblast differentiation in stressed fibroblast populated collagen lattices (FPCL). The ability of cells to contract gels, the % of cells incorporating α-SMA into stress fibers, as well as α-SMA and CTGF levels (determined by western blot analysis) are analyzed. To determine if the Col3 CR domain attenuates resistance to apoptosis in Col3-deficient cells, it is added daily to cultures of Col3+/+ and Col3−/− fibroblasts cultured in the presence and absence of TGFβ1. When the cells reach ~80% confluence, apoptosis is induced by serum deprivation for 48 hours and assessed for Annexin V and PI+/− cells by flow cytometric analysis and activated Caspase 3 staining.
Determine Whether the Col3 Triple Helical Domain Regulates Myofibroblast Differentiation and Mechanotransduction in an α11β1-Integrin Dependent Manner To determine if Col3-deficiency promotes myofibroblast differentiation in an α11β1-dependent manner, the stressed FPCL assay described above is used with the modification that Col3+/+ and −/− fibroblasts are transfected with either siRNA to murine α11 or non-targeting mock siRNA (Dharmacon, 319480), prior to seeding in collagen lattices. Collagen gels are made using rhCol1 and rhCol3 (Fibrogen), which lacks the CR domain, or a 50:50 mixture. Myofibroblast differentiation and function are assessed. Western blot analysis for α11 is performed on cell lysates to confirm knock-down. As both mechanotransduction-mediated matrix remodeling and myofibroblast differentiation are mediated through PI3K/Akt-dependent and -independent focal adhesion kinase (FAK) activation, it is determined if Col3 suppression of α11 integrin expression downregulates FAK/ERK and/or PI3/Akt signaling. Finally, to determine whether Col3 directly regulates itgα11 expression, a previously characterized α11 promoter-luciferase construct to transfect Col3−/− fibroblasts is used. Transient co-transfections are performed and luciferase activity is measured. Cells are cultured on rhCol1, rhCol3, or decellularized matrix prepared from Col3+/+ and Col3−/− fibroblasts. The TGFβ signaling inhibitor, SB-431542, is used to determine whether mechanical or biochemical features of a Col3-poor environment predominate in driving itgα11 expression.
Determine Whether the CR Domain Potentiates the Anticancer Properties of Col3-containing Biomaterials on TNBC Invasion, Migration and Apoptosis in vitro.

To determine if CR domain inclusion in Col3 biomaterials increases anti-cancer effects, a panel of 17 commercially available TNBC cell lines (ATCC) are used to examine apoptosis, migration and invasion, representing 7 TNBC subtypes. For apoptosis and migration assays, rhCol3 is used to pre-coat culture wells or transwells, respectively, and the CR peptide or control peptide is added to the media. For invasion assays, rhCol3 and the appropriate peptide are added to the MATRIGEL® prior to transwell coating and subsequent cell seeding. Col1 and no collagen controls are assessed and all assays are performed in triplicate.
Test the Efficacy of Col3 Biomaterials in Suppressing Local Recurrence and Metastasis in vivo.

To test the hypothesis that Col3 biomaterials can suppress local recurrence and metastasis in vivo, a novel composite nanofibrous collagen scaffold, is used to increase local concentrations of Col3 (200 pg/incision). These electrospun composite scaffolds consist of a biomimetic fraction (Col3) together with a slow-degrading polycaprolactone (PCL) component that provides a structural backbone and a water-soluble, sacrificial poly(ethylene oxide) (PEO) that improves cell colonization and integration of the scaffold at the excision site, effectively localizing and stabilizing the Col3 factor and providing a provisional clinically applicable product. If the addition of CR peptide is deemed advantageous, CR peptide would be incorporated into the constructs. The ability of Col3 biomaterials to control local recurrence is examined in both 4T1-Col3 model as well as a human breast cancer (GFP+MDA-231) xenograft model. Tumor cells are injected in the right 4th mammary fat pad of female Col3+/+ and Col3+/− (with 4T1), or NSG (with GFP+MDA-231) mice, as described above, and resected two weeks later to remove all gross evidence of tumor using a standardized incision to ensure a similar wound size in all mice. Establishment of single tumors in mice is performed to avoid the cross over effect that one treated tumor may have on the contralateral side. No scaffold, collagen free scaffolds (PCL/PEO only) and Col1 containing composites serve as controls (N=9 mice/group). A fifth group, in which CR is incorporated into the Col3-containing scaffold is included, if indicated. Mice are monitored for local regrowth, infection, and complications from healing. Tumor recurrence, if present, is quantitated weekly for up to 16 weeks. Mice are humanely euthanized if tumor volume exceeds 2 cm$^3$. At 16 weeks, healed incisions with or without macroscopic tumor growth are harvested for histologic assessment of local neoplastic recurrence and quality of wound repair. Pulmonary metastasis is assessed. In GFP+ MDA-MB-231 xenograft mice, peripheral blood and bone marrow are analyzed for GFP+ disseminated tumor cells (DTCs) by FACS analysis. In recurrent tumors, it is examined whether exogenously applied Col3 diminishes tumor proliferation and/or increases apoptosis in vivo using immunofluorescence for Ki67 and activated caspase-3. To determine if increased Col3 in the healing environment suppresses the formation of a tumor permissive stroma, histologic sections of recurrent tumors with surrounding margins are stained for a-SMA to determine myofibroblast density. Collagen density and TACS analysis are performed. Profibrotic CTGF levels are determined by immunohistochemistry and western blot analysis, respectively in excised primary and recurrent tumors with surrounding margins, while α11 integrin levels are assessed by western blot analysis. Compliance of the tumor stroma is measured at the tumor-stromal interface by atomic force microscopy (AFM) to determine local rheology on a submicron scale and by microindentation. Larger scale rheological measurements are also be taken. These measurements are compared to that of the nontumor bearing mammary fat pad. If Col3 application significantly reduces local recurrence and/or metastasis, a more in depth temporal analysis (2, 4, 8, and 12 week time points) in Col3+/− and NSG mice is performed to examine how Col3 (or Col3+CR and appropriate control) prevents the evolution of an aggressive TME and analyzed as described above. Finally, to determine whether Col3 therapy has any detrimental effects on wound incisional breaking strength that would impair post-operative healing, two incisions (1.0 cm each) are made in the skin overlying the mammary fat pads of immunocompetent Col3+/+ mice (N=12), implanted with or without Col3 biomaterials and harvested at 21 days post-operatively.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of suppressing metastasis and local recurrence of a cancer in a subject comprising:
   a) removing the cancer tumor from the subject; and
   b) implanting a composition to the site of tumor removed;
   wherein the composition comprises a pharmaceutically effective amount of collagen type III and,
   wherein the cancer is breast cancer.

2. The method of claim 1, wherein the subject is a human.

3. The method of claim 1, wherein the collagen type III in the composition is in the range from about 1% to about 100% by weight.

4. The method of claim 1, wherein the collagen type III in the composition is in the range from about 20% to about 80% by weight.

5. The method of claim 1, wherein the collagen type III in the composition is in the range from about 40% to about 60% by weight.

6. The method of claim 1, wherein the composition further comprises a biocompatible material.

7. The method of claim 6, wherein the biocompatible material is selected from the group consisting of alginate-poly-(L-lysine), alginate-poly-(L-lysine)-alginate, alginate-poly-(L-lysine)-polyethyleneimine, chitosan-alginate, poly-hydroxylethyl-methacrylate-methyl methacrylate, carbonylmethylcellulose, K-carrageenan, chitosan, agarose-polyethersulphone-hexadi-methirine-bromide, ethyl-cellulose, silica gels, hydrogel, (meth)acrylate-oligolactide-PEO-oligolactide-(meth)acrylate, poly(ethylene oxide) (PEO), poly(propylene glycol) (PPO), PEO-PPO-PEO copolymers, poly(phosphazene), poly(methacrylates), poly(N-vinylpyrrolidone), PL(G)A-15 PEO-PL(G)A copolymers, poly(ethylene imine), poly(ethyl glycol) diacrylate, polycaprolactone, and combinations thereof.

8. The method of claim 1, wherein the composition comprises a pharmaceutically effective amount of collagen type III, polycaprolactone, and poly(ethylene oxide) (PEO).

9. The method of claim 8, wherein the composition is prepared by electrospinning.

10. The method of claim 1, wherein the composition is in a formulation selected from the group consisting of a viscous liquid, a solution, a suspension, a liposomal formulation, a gel, a jelly, a cream, a lotion, an ointment, a suppository, a foam, an aerosol spray, an aqueous suspension, an oily suspensions, an aqueous solution, an oily solution, an emulsion, an emulsion ointment, and combinations thereof.

11. The method of claim 1, wherein the composition is formulated in a gel.

12. The method of claim 1, wherein collagen type III contains a cysteine-rich (CR) domain.

13. The method of claim 1, wherein collagen type III does not contain a cysteine-rich (CR) domain.

14. A method of suppressing metastasis and local recurrence of a cancer in a subject comprising administering a composition to the cancerous site, wherein the composition comprises a pharmaceutically effective a mount of collagen type III, wherein the cancer is breast cancer.

* * * * *